(12) United States Patent
Kauling et al.

(10) Patent No.: US 8,602,636 B2
(45) Date of Patent: Dec. 10, 2013

(54) ECCENTRICALLY-ROTATING REACTOR

(75) Inventors: Jörg Kauling, Köln (DE); Helmut Brod, Köln (DE); Sebastian Schmidt, Haan (DE); Martin Poggel, Köln (DE); Björn Frahm, Erkrath (DE); Reinhold Rose, Leverkusen (DE)

(73) Assignee: Bayer Intellectual Property GmbH, Monheim (DE)

( * ) Notice: Subject to any disclaimer, the term of this patent is extended or adjusted under 35 U.S.C. 154(b) by 705 days.

(21) Appl. No.: 12/297,987

(22) PCT Filed: Apr. 23, 2007

(86) PCT No.: PCT/EP2007/003521
§ 371 (c)(1),
(2), (4) Date: Nov. 26, 2008

(87) PCT Pub. No.: WO2007/121958
PCT Pub. Date: Nov. 1, 2007

(65) Prior Publication Data
US 2009/0180933 A1    Jul. 16, 2009

(30) Foreign Application Priority Data
Apr. 22, 2006  (DE) .......................... 10 2006 018 824

(51) Int. Cl.
*B01F 11/00*  (2006.01)

(52) U.S. Cl.
USPC ........... 366/213; 366/105; 366/107; 366/210; 366/218

(58) Field of Classification Search
USPC ......... 366/105, 107, 146, 147, 149, 208–211, 366/213
See application file for complete search history.

(56) References Cited

U.S. PATENT DOCUMENTS

| | | | |
|---|---|---|---|
| 5,057,429 A | | 10/1991 | Watanabe et al. |
| 5,110,741 A | * | 5/1992 | Ohi et al. .................... 261/122.1 |
| 5,362,642 A | * | 11/1994 | Kern ............................. 435/404 |
| 5,565,015 A | | 10/1996 | Kobayashi |
| 6,190,913 B1 | | 2/2001 | Singh |
| 6,431,745 B1 | * | 8/2002 | Schlumberger ............... 366/211 |
| 6,432,698 B1 | | 8/2002 | Gaugler et al. |
| 6,544,788 B2 | | 4/2003 | Singh |
| 6,708,957 B2 | | 3/2004 | Cote et al. |
| 2003/0143727 A1 | * | 7/2003 | Chang ........................ 435/289.1 |
| 2005/0161038 A1 | | 7/2005 | Pinatti et al. |
| 2005/0163667 A1 | * | 7/2005 | Krause ......................... 422/102 |

FOREIGN PATENT DOCUMENTS

| | | |
|---|---|---|
| DE | 10 2004 029 709 | 1/2006 |
| EP | 1 462 155 | 9/2004 |
| EP | 1 464 342 | 10/2004 |

(Continued)

*Primary Examiner* — Walter D Griffin
*Assistant Examiner* — Timothy Cleveland
(74) *Attorney, Agent, or Firm* — Norris McLaughlin & Marcus PA

(57) ABSTRACT

The invention relates to a reactor driven in an oscillatory-rotary manner about its fixed, preferably vertical, axis, for preferably biotechnological and pharmaceutical applications. By means of its process-intensifying properties for mixing, suspension, gaseous material transport, heat transfer, irradiation and particle retention, the applicability on the industrial scale is ensured. The reactor which succeeds without a shaft seal permits particularly robust production with respect to sterile technique with avoidance of cleaning and cleaning validation required when the reactor is constructed as a single-use reactor.

1 Claim, 17 Drawing Sheets

(56) References Cited

FOREIGN PATENT DOCUMENTS

| | | |
|---|---|---|
| EP | 1 512 458 | 3/2005 |
| EP | 1 602 715 | 12/2005 |
| JP | 2002 213716 | 7/2002 |
| WO | 85 02195 | 5/1985 |
| WO | 98 13469 | 4/1998 |
| WO | 00 66706 | 11/2000 |
| WO | 02 38191 | 5/2002 |
| WO | 2004 024317 | 3/2004 |
| WO | 2005 049785 | 6/2005 |
| WO | 2005 067498 | 7/2005 |
| WO | 2005 080544 | 9/2005 |
| WO | 2005 104706 | 11/2005 |
| WO | 2005 108546 | 11/2005 |
| WO | 2005 111192 | 11/2005 |
| WO | 2005 118771 | 12/2005 |

* cited by examiner

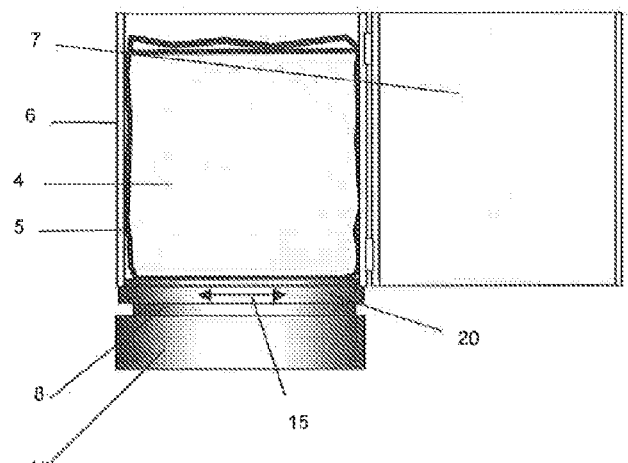
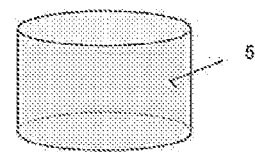
Fig. 1a        Fig. 1b
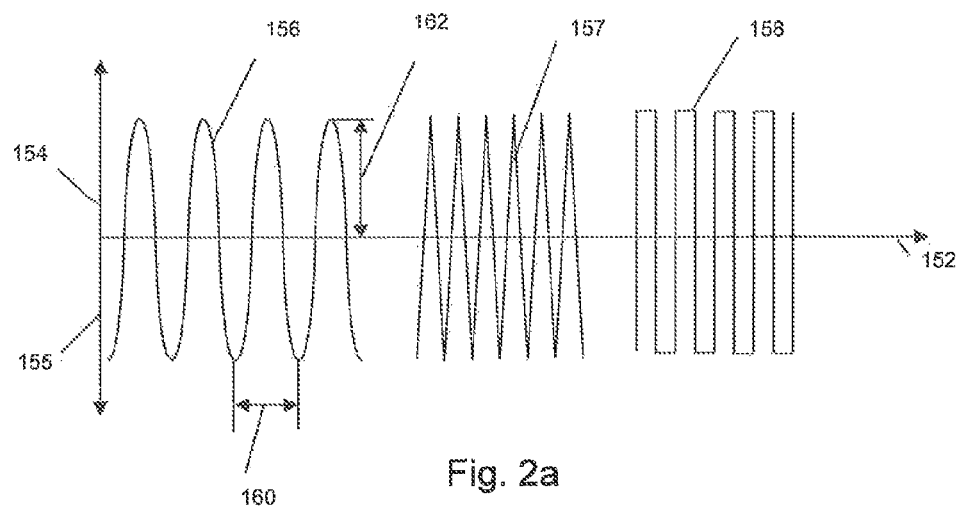
Fig. 2a

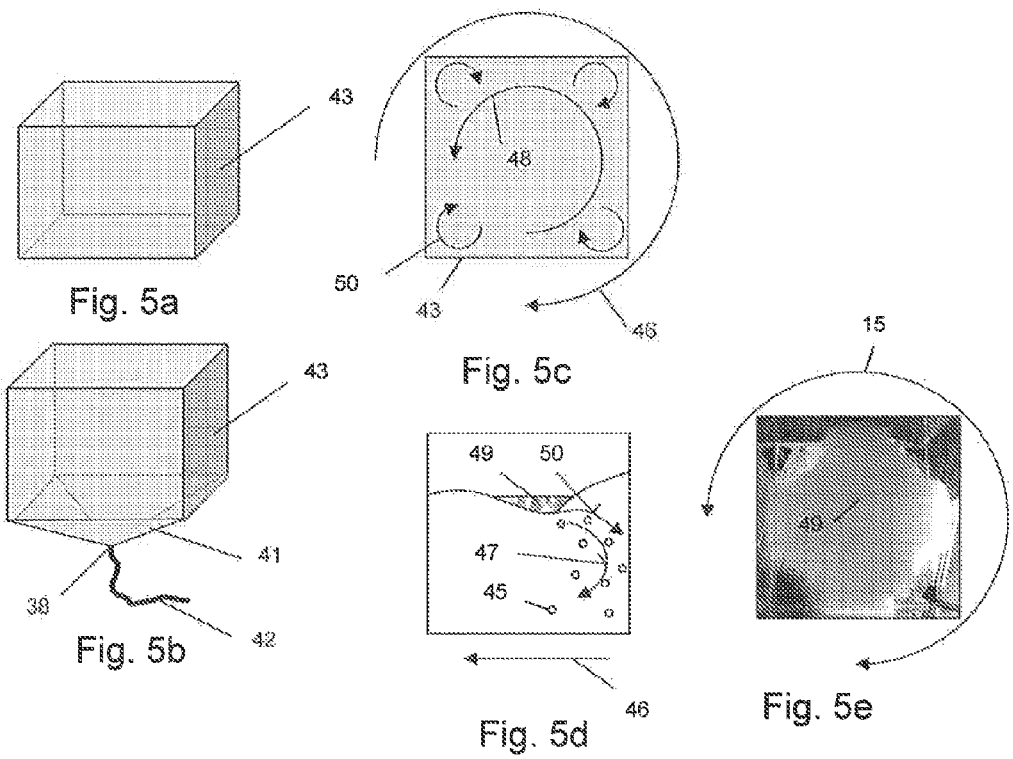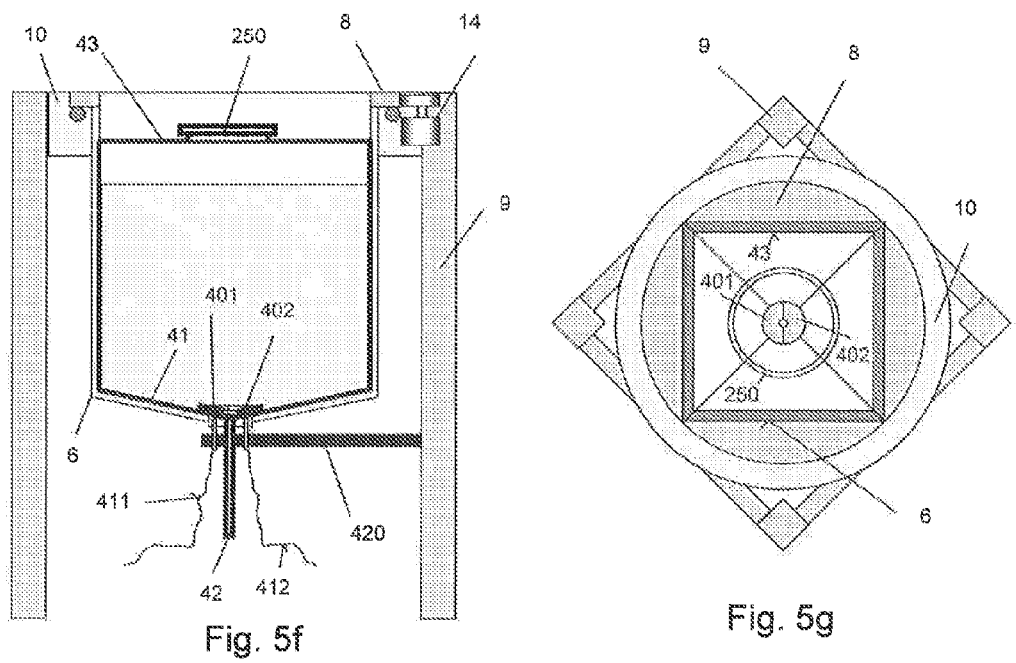

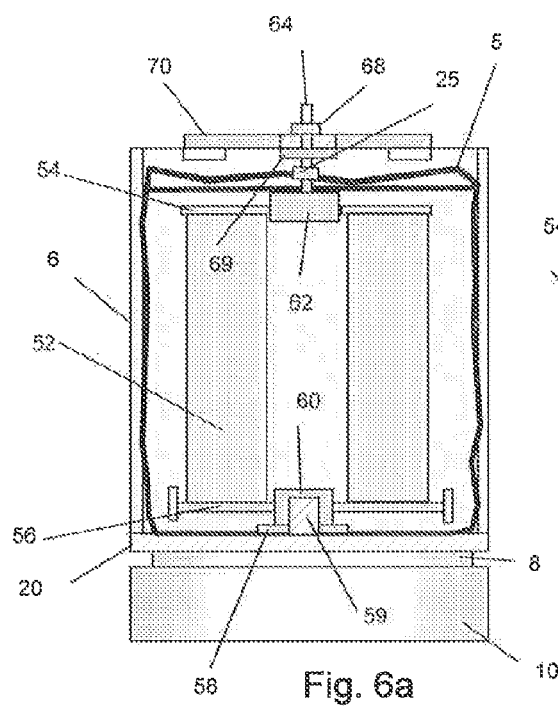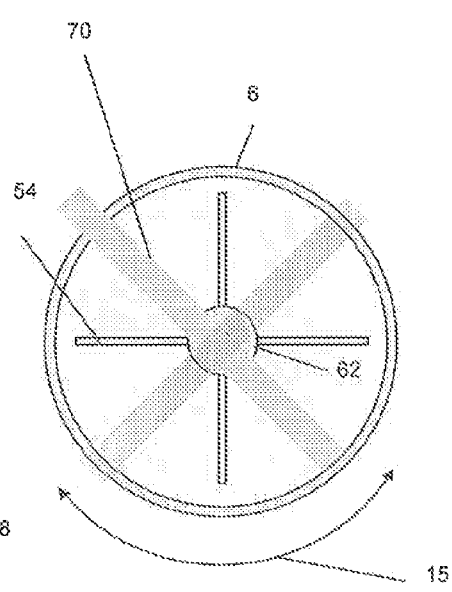
Fig. 6a
Fig. 6b

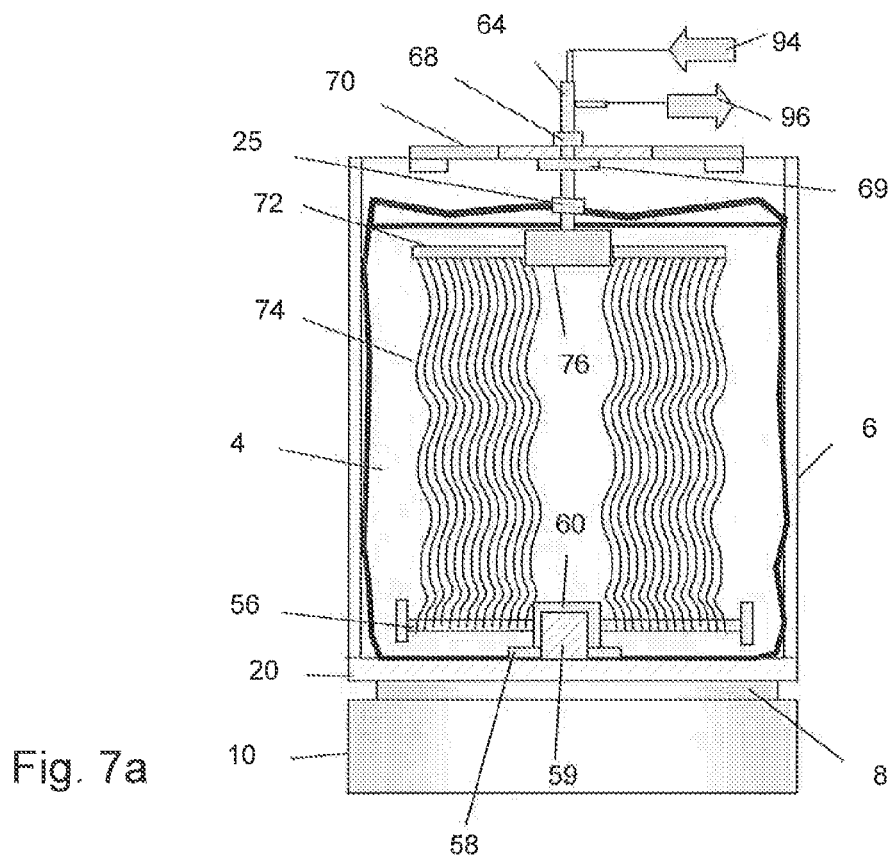
Fig. 7a
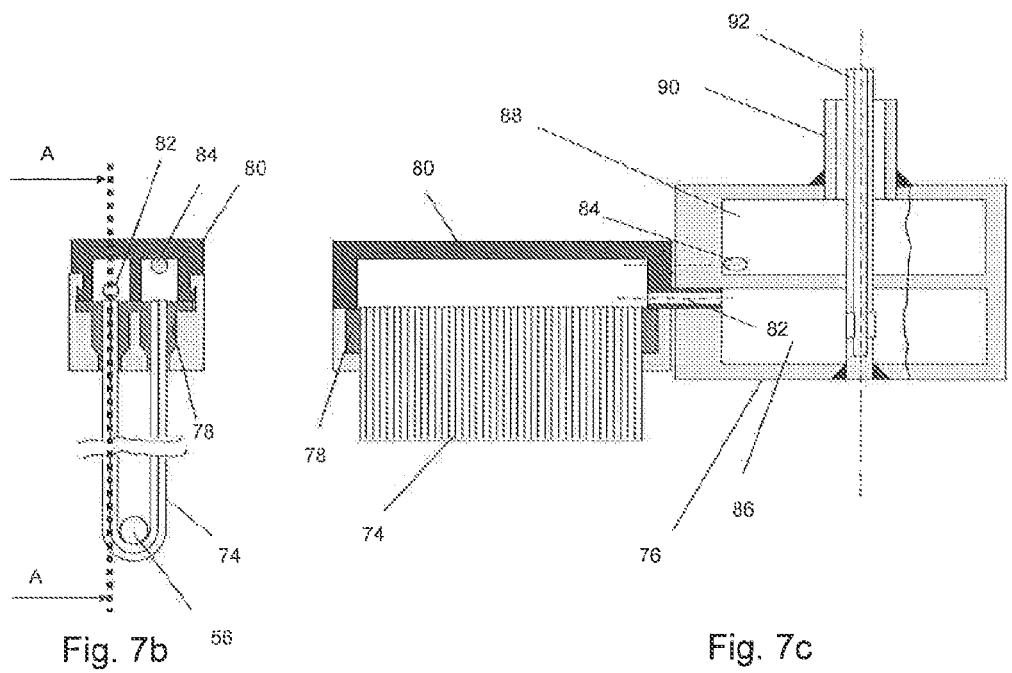
Fig. 7b
Fig. 7c

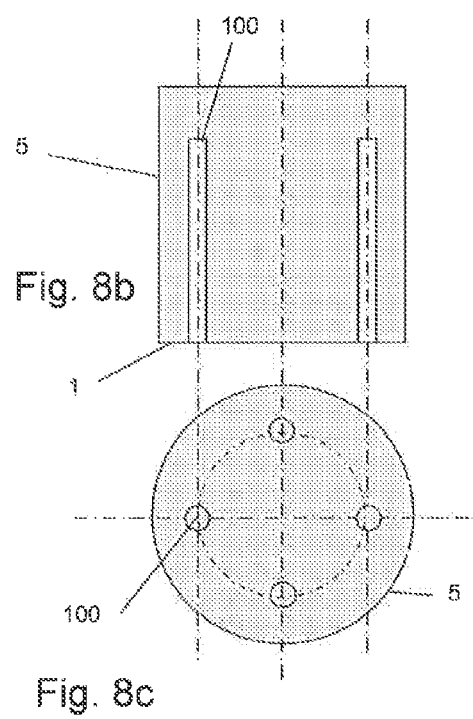
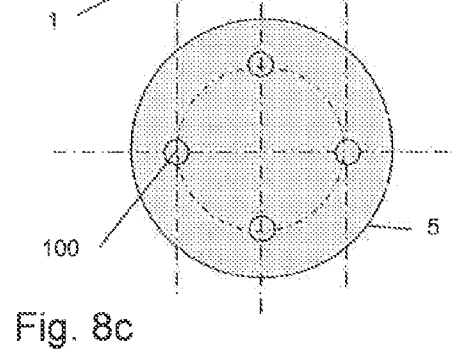
Fig. 8b
Fig. 8c
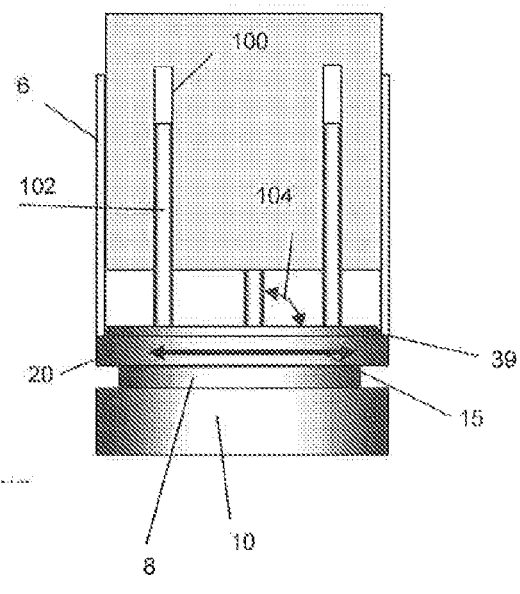
Fig. 8a

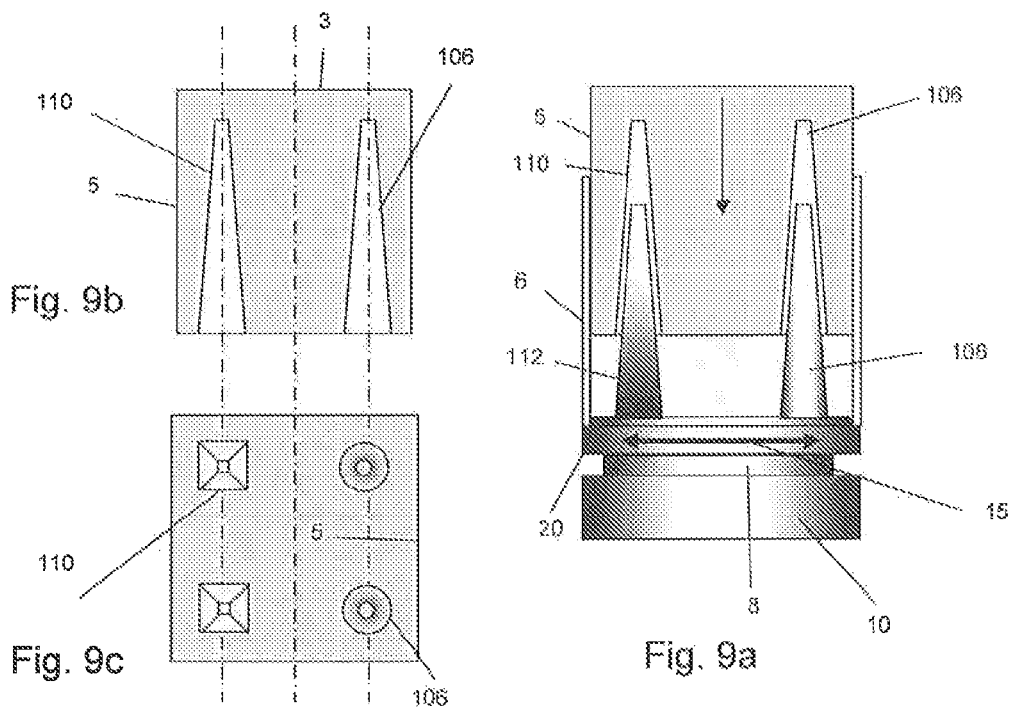

Figure 11:
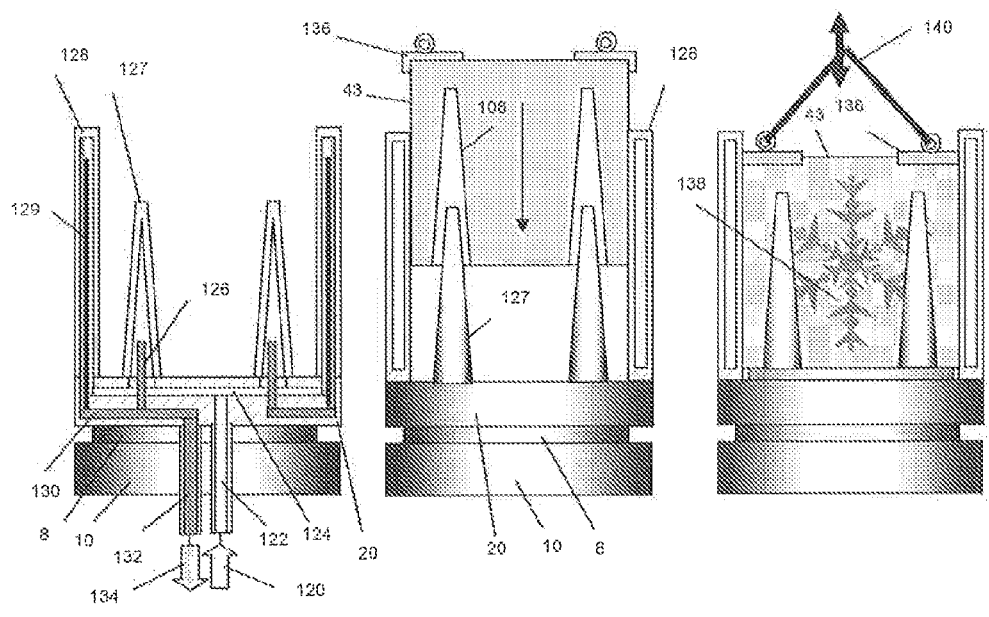

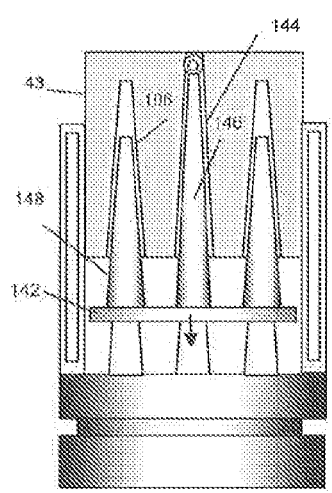 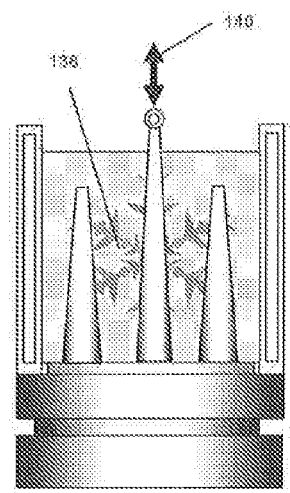 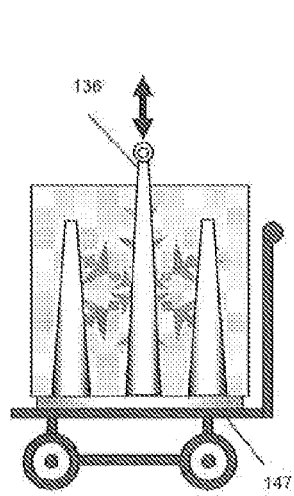
Fig. 11 d  Fig. 11 e  Fig. 11 f

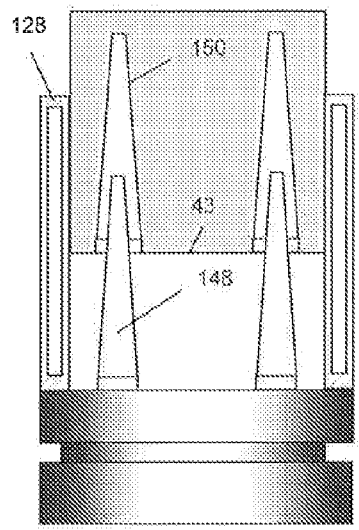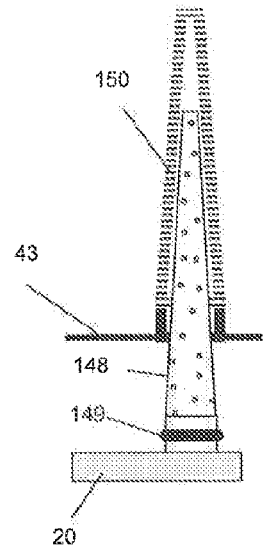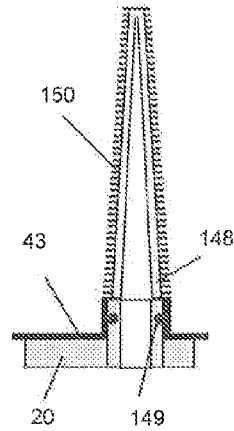
Fig. 12 a   Fig. 12 b   Fig. 12 c
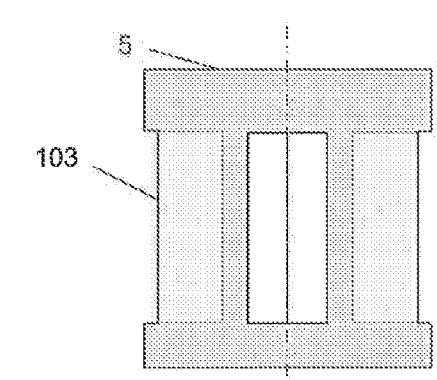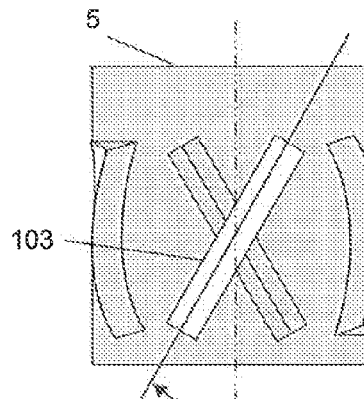
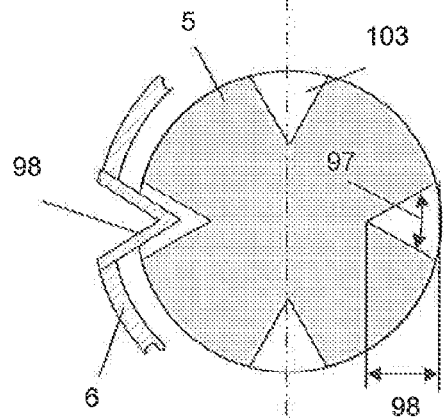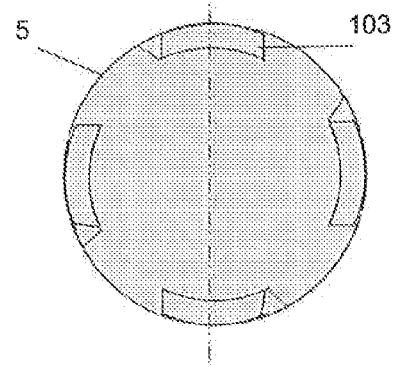
Fig. 13 a   Fig. 13 b

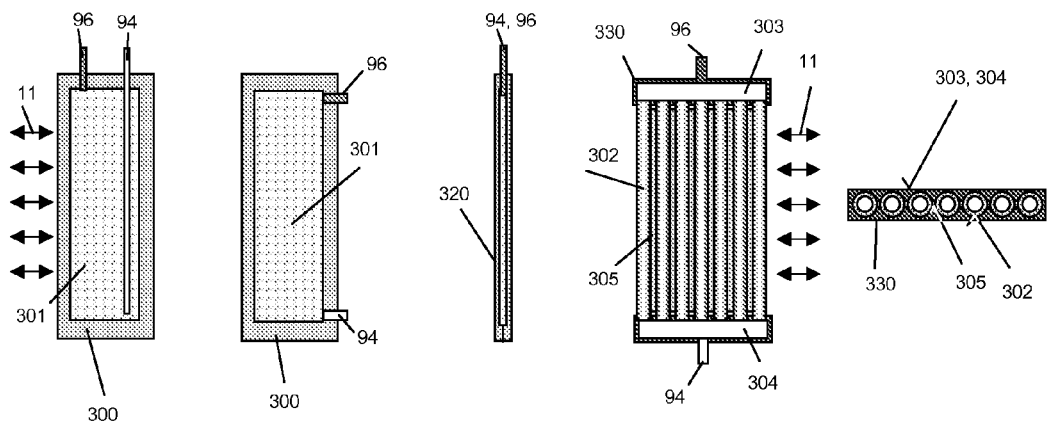
Fig. 16 a    Fig. 16 b    Fig. 16 c    Fig. 16 d    Fig. 16 e
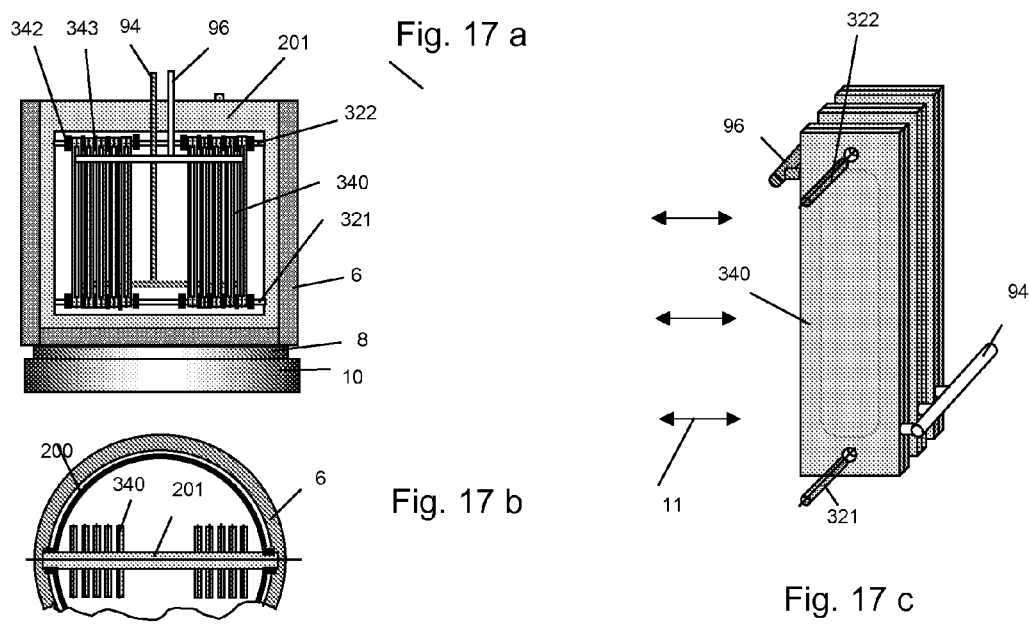
Fig. 17 a
Fig. 17 b
Fig. 17 c

ECCENTRICALLY-ROTATING REACTOR

This is a 371 of PCT/EP2007/003521 filed 23 Apr. 2007 (international filing date), which claims foreign priority benefit under 35 U.S.C. §119 of German Patent Application No. 10 2006 018 824.1 filed Apr. 22, 2006.

The invention relates to a reactor which is driven in an oscillating-rotating manner about a fixed vertical axis for biotechnological and pharmaceutical applications having process-intensifying properties for mixing, suspension, oxygen transport, heat transfer, irradiation and particle retention, which can be used, without shaft sealing, preferably as a disposable reactor, and thereby ensures a maximum level of process security in terms of cleaning and sterility.

BACKGROUND OF THE INVENTION

In the highly regulated production of pharmaceuticals, a large expenditure in terms of time, equipment and personnel is apportioned to the provision of cleaned and sterilized bioreactors. In order to avoid cross-contamination reliably in a product change in a multipurpose plant or between two product batches, apart from the cleaning, a very complex cleaning validation is required which may need to be repeated in the event of a process adaptation. This applies not only to upstream processing, USP, that is to say the production of biological products in fermenters, but also to downstream processing, DSP, that is to say purification of the fermentation products. In USP and DSP, use is frequently made of kettles as agitator and reaction systems. Especially in the case of fermentation, an aseptic environment is essential for successful culturing. For the sterilization of batch or fed-batch fermenters, generally the SEP technique is used. In order in the case of continuous process procedure to ensure sufficient long-term sterility, the autoclave technique is also used, which however, requires laborious transport of the reactors to the autoclave and is only usable with comparatively small reactor scales. The risk of contamination during fermentation is particularly critical during sampling and at moving stirrer shafts. The latter are generally equipped with complex sealing systems (e.g.: sliding-ring seals). Technologies which succeed without such penetration of the fermentation casing are preferred because of their greater process robustness.

The downtime of the reactors necessitated by the preparation procedures can be, in particular in the case of short use periods and frequent change of product, of the order of magnitude of reactor availability. The affected steps in the USP of biotechnological production are the process steps of media production and fermentation, and in the DSP, solubilization, freezing, thawing, pH adjustment, precipitation, crystallization, buffer exchange and virus inactivation.

For carrying out the reactions in the USP and DSP, frequently a plurality of reaction conditions must be met simultaneously. For instance, fermentation, for example, in addition to oxygen supply and $CO_2$ removal, requires gentle suspension of the cells, rapid mixing of the media and neutralizing agents for avoidance of overconcentration and also heating of the reaction liquid. Particle retention can also be required, e.g. for the use of perfusion strategies.

In the case of precipitation and crystallization, rapid addition of the precipitant, efficient temperature control and gentle holding of the particles formed in suspension are of particular importance.

Generally, in all process steps of biotechnological production, shallow temperature gradients are required in order not to damage the products. This condition, especially in freezing and thawing processes, leads to considerably increased process times with increasing reactor scale, since no mixing elements can be used in these steps. Heat transport into the reaction medium is limited by the thermal conductivity of the ice layer and also by free convection in the liquid. Long process times, however, can lead to considerable product losses in the presence of proteolytic activity.

Gentle sterilization and virus inactivation of starting materials and product solutions can be achieved by UVC irradiation at a wavelength of 254 nm. The radiation damages the DNA and RNA which lie at the absorption maximum of the viruses and microorganisms and prevents thereby their multiplication, whereas the proteins which are situated in the absorption minimum of the UVC radiation are very substantially retained. A great problem is the depth of penetration of the UVC radiation, which is frequently restricted to only a few tenths of a millimeter in biological media. This makes efficient replacement of the film in the active irradiation zone necessary in order firstly to irradiate all viruses with the required radiation dose and secondly to minimize the radiation load of the products.

The requirement of a constantly renewed boundary layer is also posed in the case of filtration, in order to counteract the development of covering layers which limit the transmembrane flow.

All process engineering steps of mass transport and heat transport, particle separation, UV irradiation and the addition or distribution of solids or additives or gases requires sufficient agitation of the reaction medium. This agitation is ensured, in the pharmaceutical industry, in the stainless steel reactors customarily used there, by means of appropriately dimensioned agitators or by sparging.

Membrane gas introduction is used for gentle oxygen supply of cell cultures. As membranes, gas-permeable silicone tubes are wound onto a cylindrical membrane stator which receive flow from a radially-transporting anchor agitator [WO 2005/111192 A1]. A more than doubling of the exchange area and thereby a significant increase in mass transport can be achieved by paralleling the membrane stators.

Other membrane gas-introduction systems [WO 85/02195 and DE 10 2004 029 709 B4 and DE3428758], in the gas introduction, set up agitators or baskets which are covered with membrane tubes and are moved in a pendulum-like manner in the fermentation solution, or membrane stacks [U.S. Pat. No. 6,708,957 B2], which are swung in the fermentation solution. These membrane gas-introduction systems, however, are distinguished in that they can only be converted to an industrially relevant scale with limitations.

In order to meet the demand for a rapid and flexible charging of the production plant while maintaining maximum cleanliness and sterility, designs for single-use reactors are the subject of constantly growing interest on the market.

Single-use technologies for filtration have long been known. Recently, a single-use technology has also become available on the market for UVC treatment [WO02/038191 WO02/0385502, EP1464342]. Designs for single-use heat exchangers are only available for small scales [EP1464342]. All technologies are operated in continuous flow, so that in addition to a reservoir vessel, the use of pumps and lines is necessary for which cleaning and sanitation plans still need to be provided as before.

There currently exist various commercially available mixing systems which operate on the basis of a plastic bag— single-use technology. These include systems [Hyclone Laboratories, Inc. (http://www.hyclone.com)] which are equipped with blade or magnetic stirrers or circulation pump elements. The systems are available up to a volume of 200 L.

[Sartorius AG (http://www.sartorius.de)] offers a single-use system which operates up to a volume of 500 L using a free-floating single-use magnetic stirrer which has no contact with the single-use plastic bag and therefore also no material wear. Single-use mixing systems up to a volume of 10 liters are available at [ATMI, Inc (http://www.atmi-lifesciences.com)]. In this system the material to be mixed is charged into a single-use bag and mixed under rotation. For larger volumes up to 200 L [ATMI, Inc.] offers a single-use bag stirring system which is distinguished in that the stirring element is invaginated into the bag. Mixing in this case is not achieved by a rotary motion around a fixed axis but by a stirring-tilting motion.

In [EP 1 462 155 A1], use is made of a single-use vessel for mixing and dispersing materials by means of a magnetic stirrer which is situated within a protective cage in order to prevent damage to the plastic bag. The product-contact region of the magnetic stirrer unit in this case likewise consists of single-use components.

[EP 1 512 458 A1] demonstrates a solution in which inflatable plastic pillows are integrated in the external or internal region of a single-use bag system. These pillows are alternately pressurized and depressurized again. This induces liquid movements which lead to intensification of mixing and suspension in the vessel.

There are a multiplicity of patents for the use of single-use technology in the fermentation technique sector. In these, in most systems mixing and oxygen supply are achieved via sparging, without further mixing systems being provided [U.S. Pat. No. 5,565,015, WO 98/13469, U.S. Pat. No. 6,432, 698 B1, WO 2005/049785 A1, EP 1 602 715 A2, WO 2005/080544 A2]. If a higher oxygen demand is necessary for the culture which cannot be achieved alone via sparging, the sparging can be combined with a dispersing mixing system [WO 2005/104706 A2, WO 2005/108546 A2, WO 2005/118771 A2] or can be overlapped by pumped circulation [WO 2005/067498 A2]. The maximum process volume of a sparged unit is currently up to 1000 liters. In systems having conventional agitators, but which can also be designed as single-use systems [WO 2005/104706 A2, WO 2005/108546 A2], process volumes of up to 10 000 L are achieved.

In the case of sparging, foaming problems can make the use, and the subsequent complex removal, of antifoams necessary in the DSP. The cell stress on bubble rise, in the bursting of the gas bubbles at the surface, and in particular in the foamed destruction, is problematic in cell culture systems, since the cells can be permanently damaged by the resultant high shear forces which are introduced. This applies all the more when sparging is combined with a dispersing agitating system, that is to say an agitating system comminuting the gas bubbles. The damaged cells release proteins, the removal of which can lead to considerable product losses during workup. To maintain acceptable cell vitalities, the oxygen input into the abovementioned bioreactors and therefore also the cell density which is achievable must be restricted. The restricted cell density ultimately reduces the space-time yield of the fermenters and the capacity of the total plant. Since a precondition for reliable upscaling in most cases is not considered technically as met, in the sparged single-use reactors, the volume enlargement must be achieved by complex paralleling of the systems. If the fermenters are operated as proposed using standard agitating systems, although the volume which can be processed increases into the range of the permanently installed plants, the risk of contamination can only be managed with comparable technical expenditure, for example by the use of damped sliding-ring seals. The great technical complexity and expenditure on personnel of such installations, however, largely emphasizes the advantages of the single-use concept.

Other single-use systems provide the necessary gas-introduction rate of the culture by means of membrane or surface gas introduction. In this case the necessary exchange area for gas transport is provided either via a membrane permeable to the gases to be transferred, or via an open boundary area to a gas space. Since no direct gas introduction to the cell culture media proceeds, the particle stress in these reactors may be categorized as low.

[U.S. Pat. No. 5,057,429] describes a system in which an inner semipermeable flat bag which is filled with cell suspension is surrounded by a further bag which is filled with nutrient solution and enriched with oxygen. Nutrient transport and oxygen transport are intensified via a tilting motion of the bags. The maximum process volume of a unit is only a few liters. The oxygen input is considerably restricted by the low oxygen solubility in the charged medium and the comparatively low surface area of the membrane. Compared with standard membrane gas-introduction devices [WO 2005/111192 A1] having specific exchange areas in the order of magnitude of $30\,m^2/m^3$ in 100 L reactors, in this arrangement, only a maximum of 10% of this exchange area can be achieved. In both cases, the available exchange area, furthermore, decreases in proportion to the scale enlargement.

Other surface gas-introduction systems likewise operate with a flat bag which is clamped on a shaking apparatus. The bag is only partially filled so that a free surface having a gas space lying thereabove is formed. By means of a seesawing motion or an eccentric rotary motion, the culture medium is mixed, the nutrients which are fed are distributed, cell sedimentation is prevented and the surface is agitated [U.S. Pat. No. 6,190,913 B1, WO 00/66706, U.S. Pat. No. 6,544,788 B2]. In this technology the culture is supplied with oxygen via the free surface. The motion is continuously adapted in such a manner that the flow is gentle and the cells are not exposed to strong shear. The maximum process volume of a unit is currently 580 liters. Although this technology provides a gentle gas-introduction mechanism, it is restricted in conversion to an industrial scale. The height of the bag must be kept approximately constant so that an increase in volume at constant surface area to volume ratio can only be achieved in the two horizontal spatial directions. Upscaling can therefore only be achieved via technically complex paralleling.

The technologies available on the market make use, for freezing, of large stainless steel reactors which are supplied with cooling liquids, or small flat plastic bags which are frozen in a secondary manner via heat-conducting surfaces or by means of convective cold air. In both cases there is no possibility of agitating the product during the freezing process, which considerably lengthens the cooling and freezing processes. The metal vessels are expensive and require large storage areas in the temporary storage. Thawing is lengthy, since the liquid motion between ice block and container wall proceeds only via free convection, comparably to that in freezing. For thawing the plastic bags, these are cut open in the frozen state and subsequently charged into a stirred reactor. The procedure of cutting them open is labor-consuming and contributes to fouling of the working environment. The thawing process is time-intensive, because the ice blocks which float on the surface are hardly reached by the hydrodynamics prevailing in the reactor. Product losses in the course of the long thawing phases are therefore unavoidable.

In the employment of all of the reactors listed here, considerable losses must be accepted in performance and upscalability. In many cases, without sufficient scalability, apart from the lack of performance, an economic benefit cannot be guaranteed. Scaleup here can only be achieved at the cost of increasing complexity and decreasing the economic benefit, such as, for example, by paralleling a plurality of reactors or by the additional use of technically complex solutions (for example sliding-ring seals built into the plastic bags).

A reactor which can be scaled up to the industrial scale of 1 $m^3$-10 $m^3$, guarantees a very high level of sterility comparable to autoclaving by avoiding shaft seals and the problems of cleaning, permits simultaneously intense and gentle liquid motion and can be installed with low expenditure on equipment and personnel, is therefore a clear gap in the currently available range of technologies.

It was an object of the present invention to produce a reactor, in particular for pharmaceutical applications, which, even on large reactor scales, has very good reaction properties for carrying out biological, biochemical and/or chemical reactions with respect to mixing, distribution, suspension, solubilization, mass transport and heat transport, filtration and irradiation, or combinations thereof, and is preferably simple in handling, meets the high requirements of the pharmaceutical industry with respect to cleaning and sterility and contributes to increasing process robustness and to increasing the space-time yield.

SUMMARY OF THE INVENTION

The object was achieved by a reactor comprising a reactor vessel and a drive unit, characterized in that the reactor contents, which can be taken up by the reactor vessel, are set in oscillatory-rotary motion about the fixed, preferably vertical, axis of the reactor by the drive unit, wherein the mechanical power input into the reactor contents is enabled by a suitable shell form of the reactor and/or the reactor vessel and/or by internals installed statically in the reactor and/or in the reactor vessel. The reactor is preferably constructed as a single-use reactor.

DETAILED DESCRIPTION

By means of the internals, distribution processes and/or mixing reactions can be carried out in a simple manner and with the same intensity as in a conventional stirred tank. In this design, a shaft passage can be dispensed with completely. The internals again may be supplied with material streams or energy streams via the side facing away from the product, which streams are introduced into the medium or discharged therefrom by diffusion, convection, heat conduction and/or radiation. In this manner, for the first time, in addition to mixing, numerous process engineering unit operations such as gas distribution, oxygen input by means of membrane gas introduction, heat transport, irradiation and/or particle retention can be carried out in a single-use reactor in a gentle manner and with an efficiency comparable to a stirred tank. The reactions and transport processes proceed in this case directly at the internals. Therefore, the sites of the greatest hydrodynamic energy density and greatest reactivity are identical, or in the case of reactions within the membranes, at least spatially close. No further installations (for example agitators or pumps) are required for transport of the fluids to the reaction site. Since the amount of energy introduced into the liquid is only that which is actually required for carrying out the reaction, these reactions can consequently be carried out in a particularly low-shear manner.

The latter is of critical importance, in particular in the case of shear-sensitive cultures having animal or plant cells which, e.g. during fermentation, must be supplied with oxygen. Because of the high shear forces, here sparging frequently cannot be used, so that generally low-shear membrane gas-introduction is employed. When the static mixing elements in the reactor according to the invention are constructed as tube modules, as described hereinafter, a very high oxygen input or $CO_2$ removal can be ensured using a specific tube or exchange area of more than 30 $m^2/m^3$, which is significantly enlarged compared with the prior art, in a single-use reactor without rotating sealing elements, even at large reactor scales.

The reactor has, in particular, a ratio of height to mean diameter of 0.2-2.0, preferably 0.6-1.2 and particularly preferably 0.8-1.0. As a result, tilting moments caused, e.g. by unbalanced masses, can be reduced and a possibility of operation from above is ensured, despite an erection space requirement which can be achieved without problem even on a large scale. In contrast to the slim reactors introduced in biotechnology, such a broad reactor design offers the possibility of dispensing with accommodating reactors in expensive high-rise buildings in favor of erection in cheaper shed-shaped facilities.

Preferably, internals installed in the reactor vessel are provided which provide functionalized surfaces oscillating relative to the drive unit for carrying out physical, biological, biochemical and/or chemical reactions at and/or in membranes. The functionalized surfaces can be provided, in particular, for gas introduction via semipermeable membranes, for gas distribution, for liquid distribution, for irradiation, for filtration, for absorption, for adsorption, for analysis and also for cooling and/or heating.

The invention further relates to a gas-introduction module suitable for such a reactor, in particular a gas distributor or a membrane module which are, in particular, a part of the reactor according to the invention and are described hereinafter by way of example in the installed state. The membrane module which is preferably designed as a tube module has, in particular, essentially vertically arranged permeable, in particular tubular, membranes, through which gases, such as oxygen and carbon dioxide, but no liquid, can pass, in such a manner that oxygen and/or other gases can be introduced into the reactor in a low-shear manner. The membranes can be arranged to be fixed or movable in the reactor and are particularly preferably constructed in such a manner that they can be moved relative to the inert fluid, so that not only gas introduction, gas distribution but additionally also a mixed flow can be induced. In particular, a plurality of groups of membranes or membrane tubes arranged adjacent to one another are provided which provide an exchange surface area required for membrane gas-introduction. For example, the membrane module which is constructed as a tube module and the flat membranes are constructed to be essentially immovable at least relative to the reactor, and only the reactor is driven by the drive unit, in such a manner that the gas-treatment module can be provided as required without expense on construction, in particular as an additional unit which can be connected as desired.

In a preferred embodiment, the membranes are constructed so as to be microporous and permit uniform low-shear distribution of gas bubbles, in particular microbubbles, over the reactor cross section or in the reactor volume without the aid of additional agitator elements. Preferably, the microporous membranes are constructed having core widths of 0.05-500 µm which can be provided via invaginations in the base of the reactors. In this simple manner, bubble coalescence can be successfully prevented. Membranes below 0.5 µm are particularly preferred because particularly fine gas bubbles are generated and an additionally sterile barrier can possibly be dispensed with.

In a preferred embodiment of the gas-introduction module, a first holding profile and a second holding profile are provided between which an elongated, in particular tubular, membrane can be arranged so as to be lead to and fro. The membrane in this case can be arranged in a zigzag shape or a meander shape. As a result, using a single membrane, a particularly large surface area can be provided for gas introduction to the reactor contents.

Preferably, the membrane of the gas-introduction module has a membrane film which is comparatively thin with respect to the total thickness of the membrane. The membrane film is preferably connected in a two-dimensional manner to an open-pore material, such as, for example, foam. In particular, the open-pore material is at least for the most part encased by the at least one membrane film. The open-pore material makes possible uniform convective gas transport through the membrane, in such a manner that essentially the entire membrane film can be charged with gas. Since the membrane film is connected to the open-pore material, the membrane film is simultaneously prevented from being able to inflate at elevated pressures. As a result, a gas-introduction module membrane which is further developed in this manner can be operated without problems even at high pressures, so that with comparatively low material usage, a high volumetric flow rate can be provided for gas introduction to the reactor contents.

In a preferred embodiment, the gas-introduction module is at least in part a part of the reactor vessel of the reactor according to the invention. For this the reactor vessel can have at least two, in particular exactly two, subpieces, while the gas-introduction module has a frame, using which the membranes can be fastened. The subpieces can be connected to the frame, for example by adhesion, in order, together with the frame of the gas-introduction module, to be able to form the reactor vessel of the reactor. For example, two shell-shaped subpieces are provided which, at two end sides facing away from one another of a frame which is shaped essentially rectangularly, can be stuck to the frame. The sides of the frame facing the reactor contents form a part of the shell surface of the reactor vessel. Via the sides of the frame facing away from the reactor contents the membranes of the gas-introduction module can be supplied with gas, for example oxygen, without throughlines needing to be provided therefor, which throughlines would have to be passed through the subpieces.

Preferably, the reactor vessel is lined on an inside at least in part with a permeable membrane for gas introduction to the reactor, in order to improve the gas introduction and avoid dead water zones or laminar boundary layers of the flow. For this, it is, in particular, sufficient merely to form the side of the membrane facing the reactor contents by a membrane film.

Further fields of application for low-shear reactors are precipitation or crystallization of proteins. These operating steps sometimes arise in combination with heat exchange, for example in the plasma fractionation of animal and human blood plasma, and protein purification. In both processes, a particle size distribution which is narrow and shifted to the largest possible particle diameters is required in order to avoid blockage problems and product losses in subsequent particle separation. If the internals are used in whole or in part as distributor layers for the more uniform distribution of the precipitants in the reactor space, over-concentrations may be substantially avoided which contribute to seed formation and thereby to generating very small particles. In addition, the axially transporting, eccentrically arranged, agitating elements in the precipitation reactors which are generally preferred for the macromixing may be avoided, which elements have a particularly intense shearing action on the particles. The reactors, on the product-contact side, are fabricated from materials which are known to those skilled in the art and are stable to solvents and dissolved substances.

Stability to dissolved substances is likewise an important requirement in protein solubilization. The chemicals used therefor in part have the disadvantage of attacking the stainless steel surfaces of standard reactors. The novel reactor concept according to the invention offers the alternative of a broad range of inert materials which is known to those skilled in the art.

A further reaction which can be carried out in the novel mixing reactors is irradiation of the reactor contents for the purpose of sterilization and virus inactivation. Irradiation proceeds within the single-use reactor, e.g. by means of UV irradiators which are positioned in the vessel wall and/or in the built-in elements. Support walls and bags are fabricated from transparent, UV-radiation-transmitting materials which are known to those skilled in the art, the support walls preferably of quartz glass, PMMA or Makrolon, and the bags can be fabricated, depending on the application, e.g., of fluoroelastomers, PMMA or Makrolon. A problem in the UV irradiation of biological media is the frequently extremely limited depth of penetration of the UV rays which, depending on the turbidity, can penetrate only a few tenths of a millimeter of the medium. The good mixing motion and the permanent intensive replacement of the media-side boundary layers means that also the reactor zones far from the boundary layer can be intercepted by the radiation, without the products being impermissibly damaged in the case of too long a residence time in the reactive zones. In this manner, sterilization and inactivation can be carried out for the first time even in single-use large reactors under sterile conditions with large degrees of microbial depletion and small product losses.

Further reactions which can be carried out in this reactor are physical, biological, biochemical and chemical reactions which proceed at least on, and in part in the interior of, functionalized membranes, for instance, for example but not as a restriction, enzymatic reactions, membrane adsorption processes or reactive extractions.

A further reaction which can be carried out by the mixing reactor is freezing and thawing which is required at various points of a biopharmaceutical process, in order to avoid, e.g., a product loss caused by time-dependent decomposition, in the expectation of a release analysis. Using the novel mixing reactor, entire product batches can be frozen, stored in a space-saving manner and thawed out in the same reactor. Freezing and thawing processes proceed in the agitated stage and therefore permit, for intensification and shortening the time of the processes, the use of higher temperature differences between the heating or cooling medium and product solution. Portioning over a plurality of bags and also manual removal of the bags by cutting them open and the fouling of the working environment caused thereby no longer occur.

By means of the process-intensifying internals, the application limits of existing single-use technologies are considerably expanded, in such a manner that the novel reactors can also be employed in scales which are considerably greater than those available hitherto.

The reactor is constructed, in particular, as a single-use reactor which can be discarded after it has been used. For this, the reactor vessel can be produced from a stable, preferably multilayer, polymer material or a polymer material which has been applied to stabilizing grid structures and supporting the intended process engineering unit operations. Preferably, the reactor vessel is connected to a housing which is at least in part adapted to the shell form of the reactor. For this, the reactor vessel which is preferably flexible and/or constructed so as to yield can be inserted and/or suspended into the vessel as a positive fit and/or friction fit. Preferably, the reactor vessel is additionally or alternatively detachably attached to the housing, in particular by reduced pressure. For example, a trough adjacent to the reactor vessel can be provided, to which trough a reduced pressure can be applied in order to fasten the reactor vessel.

Particularly preferably, the vessel and the reactor have at least in part an angular cross section, preferably biangular to octagonal, particularly preferably triangular to quadrangular cross section, and have flat (45), pyramidal (41) or tetrahedral bases.

In this case, the cross sectional shape can also alter in an axial direction over the height of the housing. For instance, the housing can, for example, be constructed in the upper region in a cylindrical or square shape and in a lower region rectangular, square, pyramidal, tetrahedral etc. By a rotary motion of the reactor vessel (46) thus designed, liquid flows (50) can be generated. In addition, the vessel can form internals within an outer wall of the vessel, by which internals the reactor can be accommodated in a non-slip manner, and which simultaneously act in a flow-baffling manner in order to improve the mixing of the reactor contents. The housing can be set in oscillatory-rotary motion about the fixed, preferably vertical, axis of the reactor by the drive unit, in such a manner that direct coupling of the drive unit to the reactor vessel itself is not required. As a result, most components can be reused, so that only the, if appropriate, specially shaped single-use reactor need be disposed of, which in principle does not require any additional mixing elements in order to achieve a low-shear mixing. Preferably, the housing is rotatably mounted, in particular suspended, so as to be movable in an essentially vertical direction. The housing, as a result, can, for example, be inserted simply into a holder or an axial bearing from the top using a crane or from the bottom by means of a lifting platform, in such a manner that for various housing or reactor vessel types the same drive unit and/or the same measurement technique can be employed.

Preferably, the reactor is positively coupled to the drive unit in such a manner that the acceleration and braking of the reactor rotation proceeds with an essentially constant angular acceleration or deceleration. As a result, the speed of rotation of the reactor changes linearly with time in each movement phase of the rotary oscillation. Control modules connected intermediately are not required in this simple reactor movement so that, for example, according to a preferred embodiment for implementation of the oscillatory reactor motion, a pendulum drive can be used. As a result, e.g. the release of electromagnetic rays which can cause, e.g., faults of sensors, can be drastically reduced. In particular, as a result of the constant angular acceleration in each phase of the oscillatory-rotary reactor motion, instantaneous peak values of the hydrodynamic shear forces on suspended particles (e.g. animal cells) are kept comparatively smaller than in other forms of motion of the reactor.

It has been discovered, surprisingly, that a comparatively small angular amplitude is sufficient for the oscillatory-rotary motion of the reactor in order to achieve good mixing and/or sufficient intensification of transport processes. In particular, it is hardly necessary to implement 3600° rotations, that corresponds to 10 rotations, of the reactor, so that structurally complex solutions for connecting the oscillatory-rotary reactor to the static surrounds (e.g. for the feed and removal of media and gases, of electrical energy and electric signals) are hardly required. The reactor can carry out an oscillatory-rotary motion in which the angular amplitude $\alpha$ is in the range $2° \leq |\alpha| \leq 3600°$, preferably $20° \leq |\alpha| \leq 180°$, particularly preferably $45° \leq |\alpha| \leq 90°$. In particular, approximately $|\alpha|=45°$ or $|\alpha|=90°$, wherein deviations of $\pm 5°$ can be present. In total, therefore, the oscillatory motion sweeps an angle of $2|\alpha|$ Experiments have found that when the power input is increased, states of motion can be established in this reactor in which gas bubbles are introduced into the reactor. For the cells which are not damaged by sparging, a very simple gas distribution can be achieved in this manner in a preferred polygonal, particularly preferably 2-4-angular embodiment of the reactor according to the invention without cost-intensive internals. Surprisingly, it has been found that unwanted foam development first, as expected, increases with increasing reactor agitation, in order, however, then after exceeding a maximum foam height to decrease again to easily manageable foam heights of a few centimeters. The cause of this highly astonishing phenomenon of this foam destruction is that in these states of motion of the liquid, not only the gas which is situated in the headspace, but also the foam itself is drawn in by the surface. The foam, by being sucked back below the liquid surface, is redissolved gently without application of shear forces, that is to say with strict avoidance of bursting of gas bubbles. In particular, a wave flow can be established by which a part of the reactor contents which are situated on the surface are transported into the interior of the reactor contents. In this preferred reactor type, therefore foam formation can be substantially suppressed and simultaneously particularly gentle and effective surface gas-introduction can be achieved. The use of the oscillating foam destroyer, however, is in no way restricted to reactors with surface gas-introduction, but, according to a particularly preferred embodiment, may advantageously be used generally in sparged reactors. Therefore, preferably, in the reactor according to the invention, in particular the intensity of the oscillatory-rotary motion can be set in such a manner that, at the surface of the reactor contents, a wave flow can be generated which transports a part of the reactor contents which are situated at the surface into the interior of the reactor contents.

In a preferred embodiment, the reactor vessel has an elongate fluorescence sensor running essentially in the peripheral direction to the axis of the reactor, using which, in particular a pH and/or an oxygen concentration of the reactor contents can be detected. For contact-free detection, an optical detection apparatus at a distance from the reactor vessel is provided, which gives off, for example, a light flash, in order to be able to determine, from the reaction of the fluorescence sensor to the light flash, the desired measured value. In particular, the detection rates and the oscillatory-rotary motion are selected in such a manner that the fluorescence sensor is optically detected at various part-surfaces. It is therefore possible to irradiate the fluorescence sensor at different points, so that bleaching of the fluorescence sensor by "photo bleaching" is prevented and the service life is significantly increased.

The invention further relates to a sparged reactor having a reactor vessel which has a polygonal cross section at least in the region of a liquid surface of reactor contents taken up by the reactor vessel, which reactor contents are charged with gas bubbles via the surface or porous membranes and, for the purpose of foam destruction, are set into an oscillatory-rotary motion such that foam on the surface of the reactor contents is transported into the interior of the reactor contents. The sparged reactor can, in particular, be formed and further developed as described above. The sparged reactor, therefore, is constructed in such a manner that, additionally, or alternatively, it can be a foam destroyer.

Preferably, a process is provided in which a reactor or sparged reactor is used which can be formed and further developed as described above. The reactor is particularly preferably used for suspending bioreactive substances. Therefore biological materials such as, for example, animal and/or plant cells and/or microorganisms, can be provided which are intended to be suspended in a liquid substrate in order, in particular with continuous addition of oxygen, to chemically react substances present in the substrate. The oscillatory-rotary motion of the reactor and the power input can, in particular, be set in such a manner that foam formation on the surface of the reactor contents is minimized. It is already sufficient for this for the oscillatory-rotary motion of the reactor to be at a comparatively small angular amplitude $|\alpha|$ of $\leq 3600°$, clockwise and anticlockwise. The reactor or the sparged reactor is used, in particular, for the preferably low-shear destruction of foam which can form on mixing and/or gas introduction. The destruction of the foam proceeds, in particular, by solubilizing the foam, which can be drawn into the interior of the reactor contents by the flow induced in the reactor vessel. That is to say the foam which is drawn in can collapse in a low-shear manner in the interior of the reactor contents.

The invention will be described in more detail hereinafter with reference to the accompanying drawings referring to preferred examples, to which the invention is not restricted.

Figure 2B:
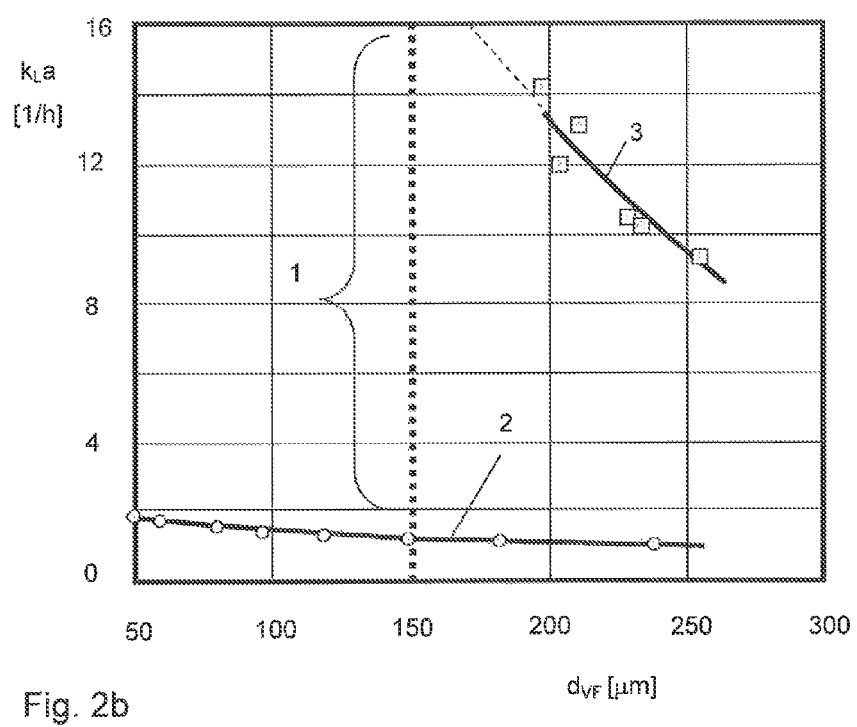
Figure 3A:
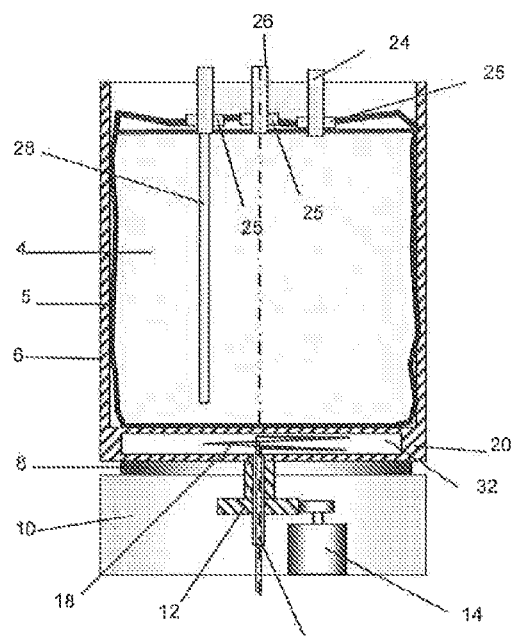
Figure 3B:
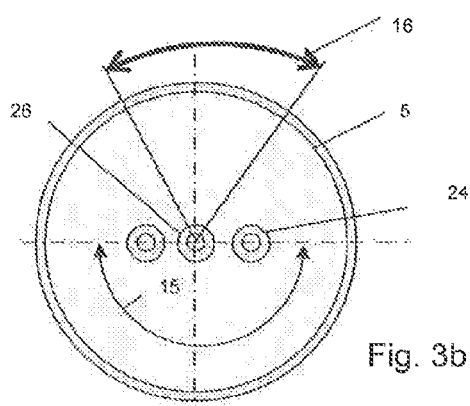
Figure 3C:
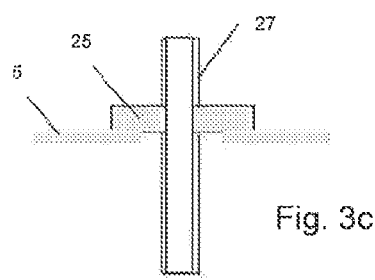
Figure 4A:
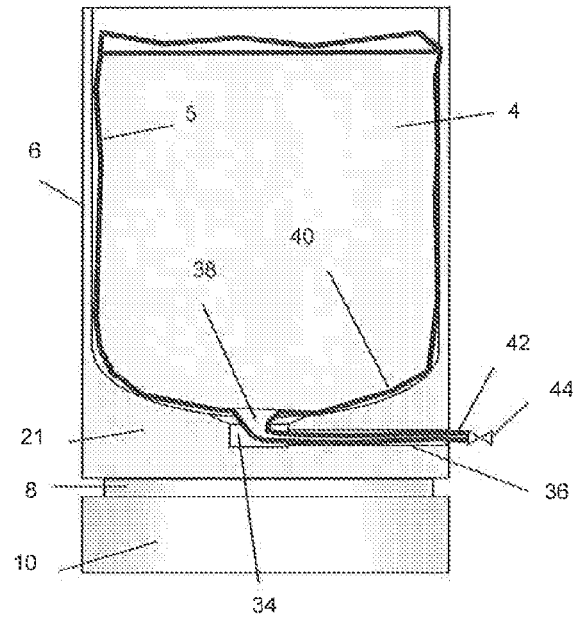
Figure 4B:
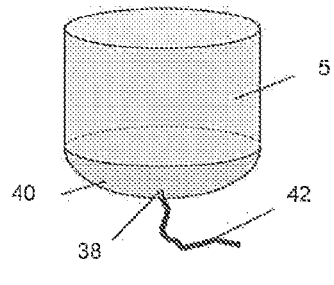
Figure 7D:
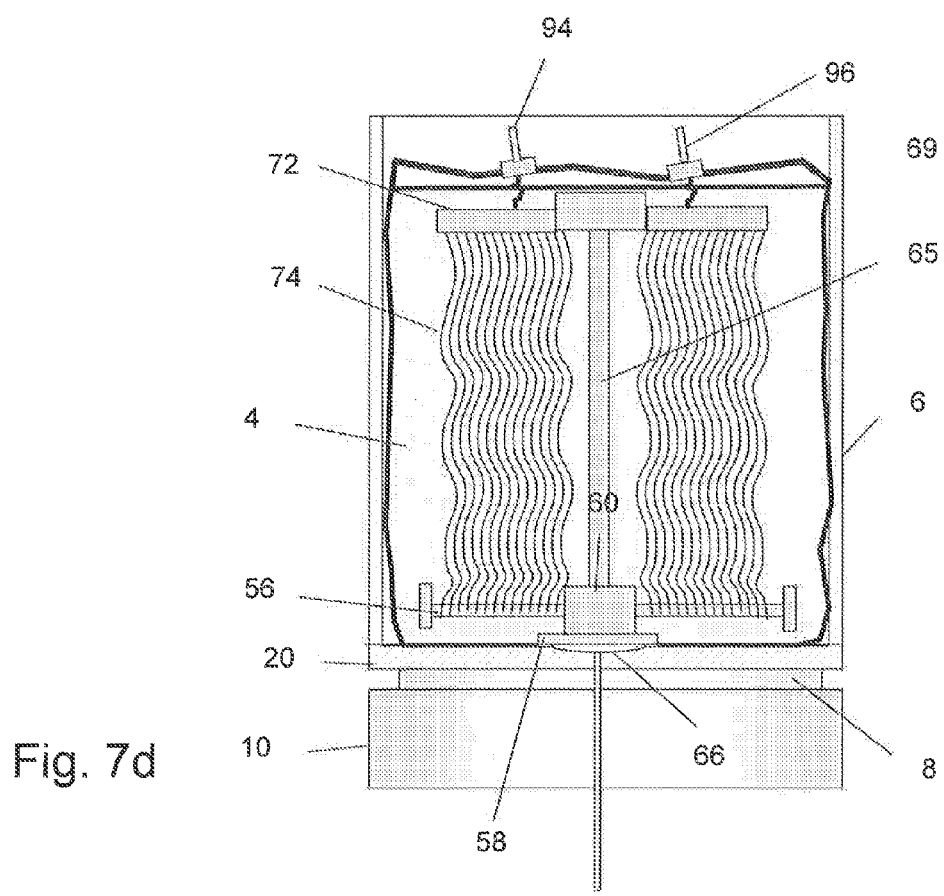
Figure 10:
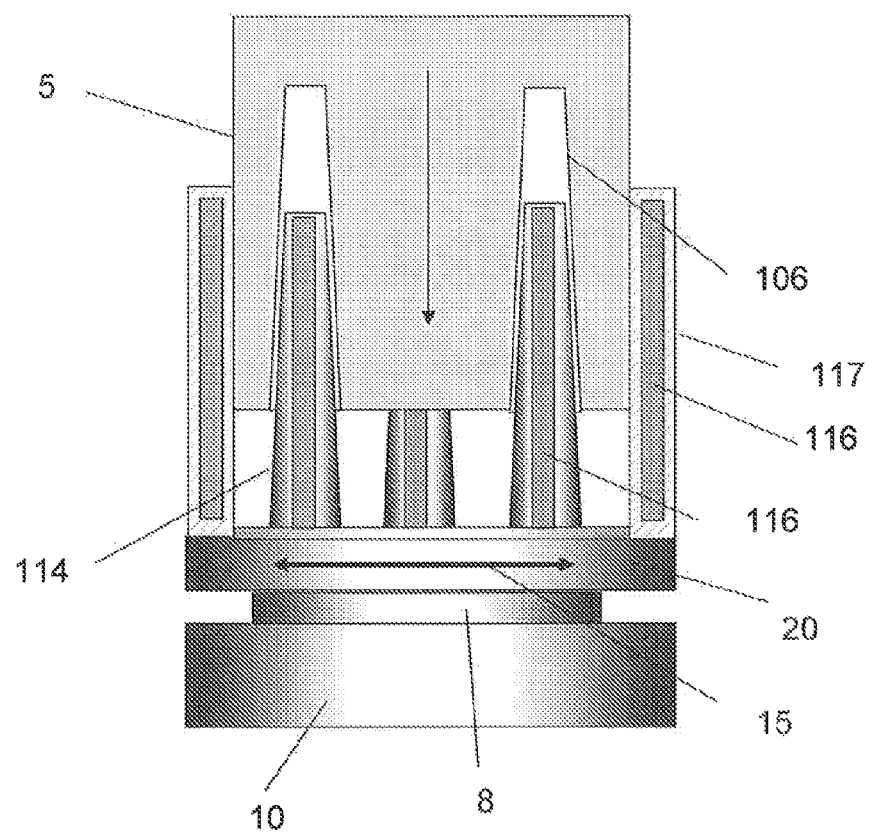

The drawings show the following:

FIG. 1a: a schematic simplified side view of an installed reactor,

FIG. 1b: a schematic perspective view of the reactor of FIG. 1a,

FIG. 2a: a schematic diagram having rotary oscillation suitable for the reactor, FIG. 2b: a schematic diagram for comparison of the $O_2$ introduction in various gas-introduction methods, FIG. 3a: a schematic side view of the reactor of FIG. 1a, FIG. 3b: a schematic plan view of the reactor of FIG. 3a, FIG. 3c: a schematic sectional detail view of the reactor of FIG. 3a, FIG. 4a: a schematic simplified side view of the installed reactor in a further embodiment, FIG. 4b: a schematic perspective view of the reactor of FIG. 4a, FIG. 5a: a schematic perspective view of the reactor in a further embodiment, FIG. 5b: a schematic perspective view of the reactor in a further embodiment, FIG. 5c: a schematic perspective plan view of the reactor of FIG. 5a or FIG. 5b, FIG. 5d: a schematic sectional detail view of the reactor of FIG. 5a at high velocities, FIG. 5e: a schematic plan view of the reactor of FIG. 5a at high velocities, FIG. 5f: a schematic sectional view of the reactor of FIG. 5a in a further embodiment, FIG. 5g: a schematic plan view of the reactor of FIG. 5f, FIG. 6a: a schematic sectional view of the reactor in the installed state in a further embodiment, FIG. 6b: a schematic plan view of the reactor of FIG. 6a, FIG. 7a: a schematic sectional view of the reactor in the installed state in a further embodiment, FIG. 7b: a schematic sectional view of a silicone tube suitable for the reactor, FIG. 7c: a schematic sectional view of a module having the silicone tube of FIG. 7b, FIG. 7d: a schematic sectional view of the reactor of FIG. 7a in a further embodiment, FIG. 8a: a schematic sectional view of the reactor in the installed state in a further embodiment, FIG. 8b: a schematic sectional view of the reactor of FIG. 8a, FIG. 8c: a schematic plan view of the reactor of FIG. 8b, FIG. 9a: a schematic sectional view of the reactor in the installed state in a further embodiment, FIG. 9b: a schematic sectional view of the reactor of FIG. 9a, FIG. 9c: a schematic plan view of the reactor of FIG. 9b, FIG. 10: a schematic sectional view of the reactor in the installed state in a further embodiment, FIG. 11a: a schematic sectional view of the reactor in the installed state in a further embodiment in a first state, FIG. 11b: a schematic sectional view of the reactor of FIG. 11a in a second state, FIG. 11c: a schematic sectional view of the reactor of FIG. 11a in a third state, FIG. 11d: a schematic sectional view of the reactor of FIG. 11a in a fourth state, FIG. 11e: a schematic sectional view of the reactor of FIG. 11a in a fifth state, FIG. 11f: a schematic sectional view of the reactor of FIG. 11a in a sixth state, FIG. 12a: a schematic sectional view of the reactor in the installed state in a further embodiment, FIG. 12b: a schematic sectional detail view of the reactor of FIG. 12a in a first state, FIG. 12c: a schematic sectional detail view of the reactor of FIG. 12a in a second state, FIG. 13a: a schematic sectional view and a schematic plan view of the reactor in the installed state in a further embodiment, FIG. 13b: a schematic sectional view and a schematic plan view of the reactor in the installed state in a further embodiment.

Figure 14:
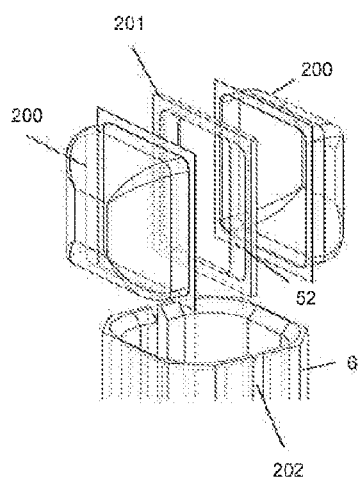
Figure 14:
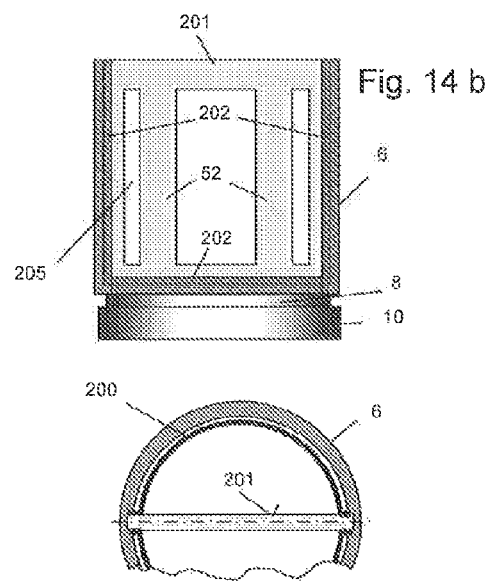
Figure 14:
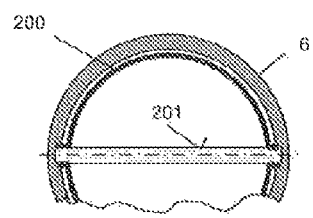
Figure 15:
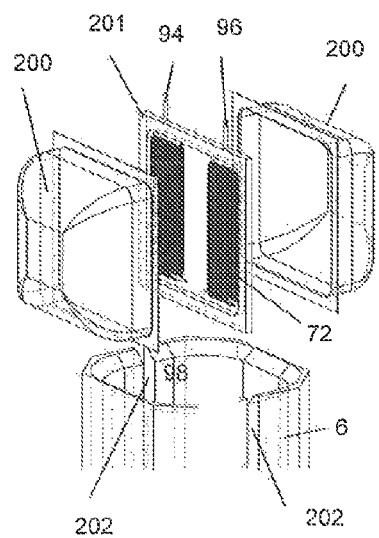
Figure 15:
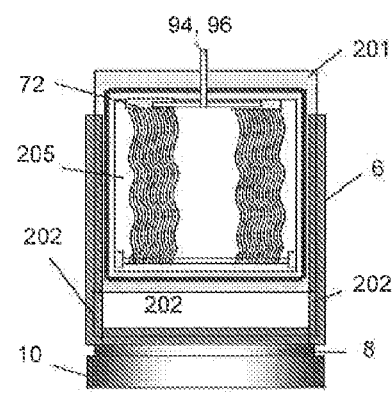
Figure 15:
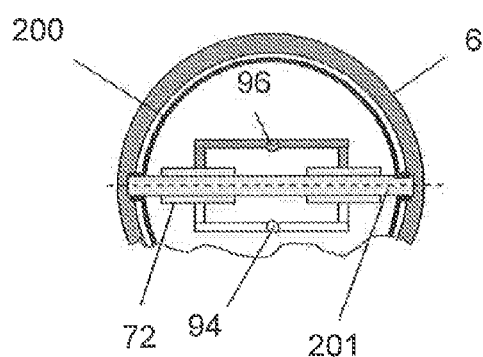
Figure 15:
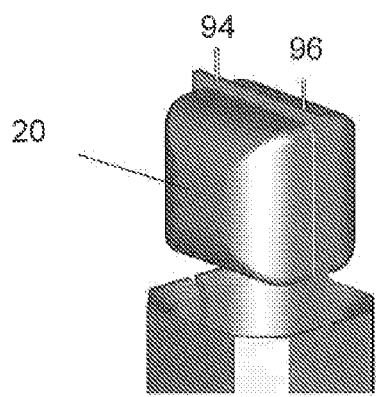
Figure 15:
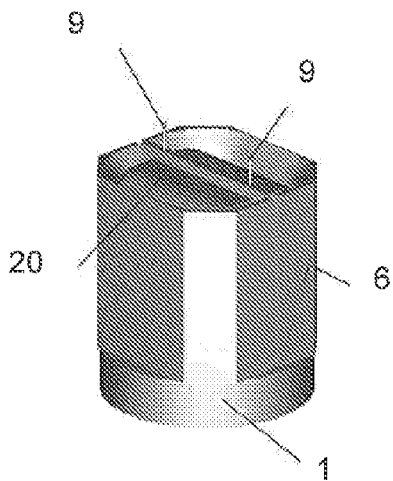
Figure 18:
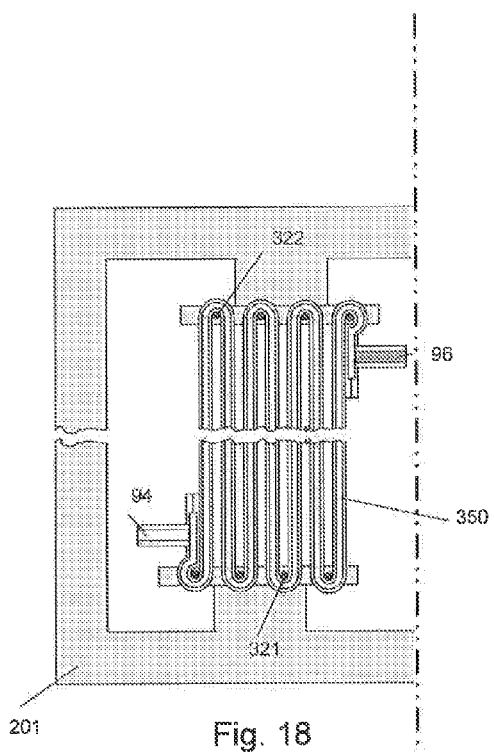
Figure 19:
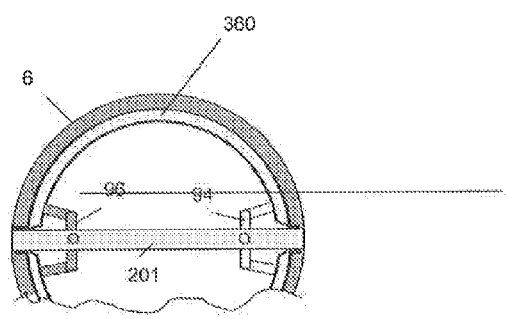
Figure 20:
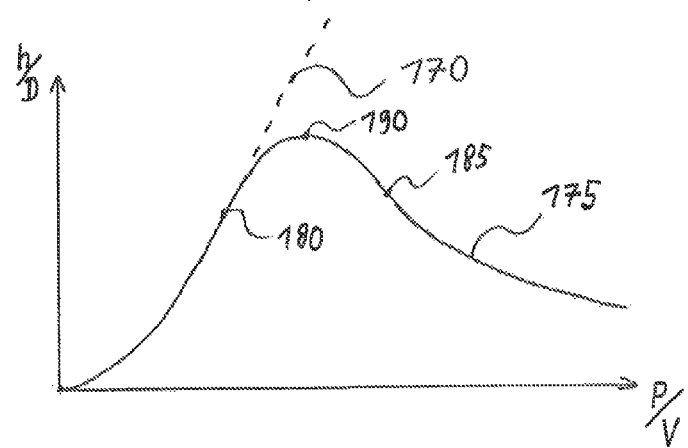

FIG. 14a: a schematic perspective exploded view of the reactor in a further embodiment, FIG. 14b: a schematic sectional view of the reactor of FIG. 14a, FIG. 14c: a schematic plan view of the reactor of FIG. 14a, FIG. 15a: a schematic perspective exploded view of the reactor of FIG. 14a in a further embodiment, FIG. 15b: a schematic sectional view of the reactor of FIG. 15a, FIG. 15c: a schematic plan view of the reactor of FIG. 15a, FIG. 15d: a schematic perspective view of the reactor of FIG. 15a before installation, FIG. 15e: a schematic perspective view of the reactor of FIG. 15a after installation, FIG. 16a: a schematic sectional view of a membrane suitable for the gas-introduction module, FIG. 16b: a schematic sectional view of a membrane suitable for the gas-introduction module, in a further embodiment, FIG. 16c: a schematic sectional detail view of the membrane of FIG. 16a, FIG. 16d: a schematic sectional view of a membrane suitable for the gas-introduction module, in a further embodiment, FIG. 16e: a schematic sectional plan view of the membrane of FIG. 16d, FIG. 17a: a schematic sectional view of the reactor in a further embodiment, FIG. 17b: a schematic plan view of the reactor of FIG. 17a, FIG. 17c: a schematic perspective view of a part of the gas-introduction module for the reactor of FIG. 17a, FIG. 18: a schematic sectional view of the reactor in a further embodiment, FIG. 19: a schematic plan view of the reactor in a further embodiment and FIG. 20 a schematically represented qualitative experimental result on foam generation following gas bubble introduction through the liquid surface with simultaneous foam destruction following suction of the foam into the liquid.

INDEX

1 Potential
2 $O_2$ transport in the case of tubular stators+anchor agitators
3 $O_2$ transport in the case of membrane modules
4 Reactor contents
5 Reactor
6 Moving housing
7 Door
8 Bearing
9 Frame
10 Drive table
11 Oscillating liquid motion
12 Drive shaft of moving housing
14 Drive
15 Rotary oscillation
16 Angle of the oscillating motion
17 Reactor width
18 Heat exchanger
20 Base
21 Domed base
24 Off-center connection port
25 Welded-in axial passage
26 Central connection port
27 Axial passage
28 Connection port with extension
30 Inlet and outlet of the heating/cooling medium
32 Heat exchanger reception
34 Base recess
36 Horizontal opening in the base
38 Central tube connection (bag)
40 Domed base (bag)
41 Pyramidal base (bag)
42 Outlet tube (bag)
43 Rectangular reactor
44 Harvesting valve (bag)
45 Gas bubbles
46 Accelerated motion
47 Flow vortex
48 Relative motion of the liquid
49 Foam
50 Radial secondary vortex
52 Agitator blade, film element
54 Top clamping element
56 Bottom clamping element
58 Base support
59 Pin for transmitting the torque to 58
60 Distributor bottom
62 Distributor top
64 Tie rod
65 Connection element
66 Suction cup
68 Tightening device tie rod
69 Lock nut tie rod
70 Holding device
72 Tube module
74 Silicone tube
76 Module holding and supply device
78 Casting compound
79 Base body
80 Module holder
82 Attachment line gas feed
84 Attachment line gas takeoff
86 Distributor space gas feed
88 Distributor space gas takeoff
90 Tie rod and supply line gas feed
92 Tie rod and supply line gas takeoff
94 Gas stream feed
96 Gas stream outlet
97 Width of the side pocket
98 Depth of the side pocket
99 Side supporting element
100 Invagination in the top or bottom
102 Cylindrical supporting element
103 Side pocket
104 Support element angle of incidence to the horizontal
105 Angle of the side pocket
106 Conical invagination
107 Tapering angle of the support element
108 Conical support element
110 Pyramidal invagination
112 Pyramidal support element
114 Radiation-transmissive conical support element
116 Radiation source
117 Irradiation shell
118 Radiation-transmissive conical invagination
120 Heating/cooling medium feed
122 Feed line heating/cooling medium
124 Distributor channel
126 Takeoff tube
127 Heatable/coolable support element
128 Heating/cooling shell
129 Reversing device
130 Collection channel
132 Outlet line heating/cooling medium
134 Heating/cooling medium outlet
136 Carrying ring with eyes
138 Frozen fluid
140 Carry cable
142 Intermediate base
144 Passage
146 Lengthened support element
147 Transport
148 Liquid-distributing support element
149 O-ring
150 Filtering layer
151 Cylindrical attachment element
152 Time axis
154 Velocity in leftward direction
155 Velocity in rightward direction
156 Sinusoidal velocity profile
157 Linear velocity profile
158 Stepped velocity profile
160 Time interval per motion cycle
162 Amplitude
170 Expected foam development in the system with surface gas introduction without foam destruction
175 Foam development following surface gas introduction with simultaneous foam destruction
180 First inflection point
185 Second inflection point
190 Maximum
200 Bag half
201 Frame
202 Groove in moving housing 203 Peripheral connection edge of the bag half
204 Frame-supported bag
205 Distance between frame and blade element
250 Lid
300 Membrane film
301 Porous layer
302 Membrane tube extruded in parallel strips
303 Distributor space
304 Collection space
305 Connection bridges between membrane tubes
320 Flow-passing element of flat membranes
321 Bottom holder
322 Top holder
330 Flow-passing element of tube membranes
340 Membrane stack
342 Boundary element
343 Distancing element
350 Meander-shaped clamped membrane element
360 Membrane element integrated into the bag wall
401 Sensor layer 1
402 Sensor layer 2
420 Holder for light conductor
411 Light conductor for sensor layer 1
412 Light conductor for sensor layer 2

FIGS. 1a and 1b show a reactor vessel, designated reactor 5, of the reactor according to the invention having a drive unit without process-intensifying internals. The medium 4, a substrate or buffer solution, a fermentation solution or a product solution, is contained in the reactor 5 which, in the case of the particularly preferred use as single-use reactor for improving stability, is produced from stable, preferably multilayer, plastic films which are known to those skilled in the art. The mass of the filled reactor 5 which, for strength reasons, can only be burdened with limited tensile and shearing forces, is taken up in the vertical direction from the base 20 of a surrounding vessel and in the side direction via the shell 6 thereof. For simple installation of the reactor 5, the shell 6 can be opened via a door 7. During the process the base 20 which is rotatably mounted on the bearing 8 is set in oscillating rotation 15 via the drive table 10. The position of the drive axle is preferably fixed in order to avoid transverse forces caused by eccentricity on the reactor 5, or the system consisting of shell 6, base 20 and drive table 10. Transverse forces pose considerable problems on upscaling. The angle of the drive axle can be chosen, in principle, as desired between 0 and 90° to the horizontal. Angles around 90° to the horizontal are among the particularly preferred embodiments, because as a result a comparatively simple bearing mounting of the reactor and the drive unit is possible. In this type of bearing, the head region of the reactor 5 remains substantially unloaded and permits a simple access to the reactor interior by connection lines and sensors. By means of a simply achieved size adaptation of shell 6 and reactor 5, smaller reactors can also be operated on the same base 20, which increases the flexibility of production, in particular in the case of frequent product changes.

FIG. 2a shows suitable rotary oscillations 15, e.g. having a rectangular 158, linear 157 or sinusoidal 156 course of angular velocity with time. The period 160 and amplitude 162 of the rotary oscillation 15 depend on the geometry and size of the reactor 5 and internals thereof and the desired mechanical power input which is required to carry out the process step. A low-shear motion can be induced when losses due to flow around the internal elements and thereby relative velocity between the internal elements and the fluid can be kept as constant as possible. In order to achieve this, the fluid is expediently first accelerated into the one direction with a sinusoidal velocity impulse 156 of the internal element and later decelerated in order, on passing through zero of the rotary velocity, ultimately to be accelerated and decelerated in the opposite direction. If the torque of the drive used permits high angular accelerations of the reactor, rectangular impulses 158 may be implemented to an approximation. However, these lead to a considerably greater range of velocity distribution in the reactor and thereby, with comparable mechanical power input, to an increase of the shear stress of suspended particles. This drive mode will generally be avoided on the culture of shear-sensitive animal cells. In the suspension of sedimented particles or on mixing in additives, these additional mixing effects, in contrast, are absolutely desired.

In the case of membrane gas introduction, high specific exchange areas of significantly more than 30 $m^2/m^3$ can be ensured in a single-use reactor without rotating sealing elements and, what is more, in very large reactor scales. FIG. 2b shows the gentle use of the membrane gas introduction 3 according to the invention using tube modules 72 in comparison with a prior art flow-fed membrane stator system 2 fed by an agitator element. To generate this diagram, the volumetric mass transport coefficient ka for oxygen was measured by the dynamic method and plotted as ordinate. On the abscissa what is termed the reference flock diameter is plotted, determined by the method described by von Henzler and Biedermann (Henzler, H.-J., Biedermann, A., Beanspruchung von Partikeln in Rührreaktoren [Stressing of Particles in Stirred Reactors], Chemie-Ingenieur-Technik 68 (1996) 1546 ff.). The reference flock diameter is a measure of the hydrodynamic shearing of small suspended particles, wherein small reference flock diameters indicate large shearing forces and vice versa. According to this investigation, the potential 1 of the power increase of the ka value is, for the same particle stressing, more than 10-fold, if, for sensitive cell cultures in the turbulent flow range, reference flock diameters of 150 micrometers are used as a basis. This enormous potential 1 makes possible a degree of play in the scaleup and in the design of inexpensive gas-introduction membranes. As an alternative to tube modules 72 with which very large specific exchange areas may be achieved in bioreactors, e.g. also cheaper flow-passing elements made of flat membranes 320 or parallel extruded tube membranes 330 having slightly reduced specific exchange areas of the order of magnitude of approximately 10 $m^2/m^3$ can also be used.

In the case of generation of coarse or fine gas bubbles via membranes, use can be made of, for example, the oscillating motion of microporous invaginations 150, in order to distribute gas bubbles in the liquid 11 uniformly over the reactor cross section.

FIG. 3a shows by way of example, but not restricting the invention, in what manner the base 20 rotatably mounted on the bearing 8 can be driven via a gear wheel 12 using an electric drive 14 which is installed in the drive table 10. Alternative drive possibilities to electric drives 14 could be provided via magnetic forces, induction forces, pneumatics or hydraulics. For heating/cooling the medium 4, the base 20 can be equipped with a cavity 32 in which an electric (for example a heating mat) or a heat exchanger 18 through which a heating/cooling medium flows can be accommodated. To improve the heat transfer it is advisable to fill the cavity 32 with a readily heat-conducting heat transfer medium, e.g. water or oil. The heat exchanger is supplied via a central line 30 which is connected via tubes or cables to the energy supply, i.e. to a heating/cooling circuit or to electricity. Addition or withdrawal to or from the reactor 5 can be performed via central 27 or offcenter 24, 28, passages through the head of the reactor 5. Using the lance 28, addition also into the depth in the reactor 5 can proceed. In the case of offcenter addition, the lance 28 acts as a flow resistance to the surrounding medium 4, so that at the introduction site, corresponding to the chosen intensity of the rotary oscillation 15, a liquid flow favoring mixing can be produced. The passageways 24, 26 and 28 are likewise suitable for bringing commercially available sampling systems and sensors for measuring temperature, gas content, ion concentration, optical properties, particle concentration and cell vitality into contact with the medium 4 or the gas space for the purpose of process control. The introduction of thermally or chemically presterilized and calibrated systems can proceed at the start of the process under a safety cabinet. The sensors are customarily fastened to the port using a screw connection and sealed to the inner flanks of the passageways by means of an O-ring. Preference is further given to sensors based on fluorescent reactive dyes which are simply applied to the reactor wall in order to interact with the medium. Excitation and measurement of the layers can proceed non-invasively from the outside, which eliminates the risk to sterility of sensor introduction. The load-bearing capacity of reactors fabricated with plastic can be increased in the region of the passageways by means of welded or glued reinforcements 25 (see also FIG. 3c). It is expedient to restrict the angle 16 (see FIG. 3b) between the two reversal points of the rotary oscillation 15. In this manner, excess torsional strain of the flexible supply lines such as, for example, tubes or electric cables, which are attached to the reactor 5 is prevented. Although angle 16 up to 3600° is not manageable technically, it has surprisingly been shown that the reactors are comparatively low shear even at significantly smaller angles 16 that and may be operated with good hydrodynamic surface flow of the internal elements provided for process intensification. Conversion of scale can, depending on the task, proceed by keeping constant the mechanical power input P/V or the particle stresses or the path lengths taken by the flow internals. It follows therefrom that, depending on the criterion used, the angular velocity and/or the angle 16 decrease with increasing reactor size 17 on scaleup.

An expedient embodiment of the single-use reactor which does not restrict the invention is shown in FIGS. 4a and b. These single-use reactors have a domed base 40 and a central outlet 38. This means that, after a valve 44 is opened, complete withdrawal of the medium is possible via a tube line 42. The tube line 42 is laid toward the outside from the conical recess 34 via a base gap 36 of the domed base 21.

A particularly simple, and nevertheless effective, method for transmitting the rotary oscillation 15 from the reactor walls to the medium 4 can proceed without flow internals, just by the choice of a suitable reactor geometry. If, as is shown in FIGS. 5a-c, instead of a reactor having a cylindrical cross section 5, a rectangular reactor 43 having a flat (see FIG. 5a) or pyramidal 41 (see FIG. 5b) base is used, this gives the secondary flows 50 shown in FIG. 5c. These are a reaction to the relative motion 48 which counteracts the accelerated rotary motion 46 of the rectangular reactor 43 and is caused by the mass inertia of the medium 4. Using these secondary flows 50, mixing operations can be initiated. As a result of the motion of the liquid surface, the reactor is also suitable for oxygen input by surface gas-introduction. Since the reactor height would have to be kept constant on scaleup, this gas-introduction method, depending on the desired cell count, is only suitable for small reactor volumes because of the considerable space requirement for erection. An improvement of oxygen input is achieved, provided this is tolerated by the cells, by sparging, which in the case of this reactor proceeds above certain states of motion dependent on the reactor scale by drawing gas bubbles below the liquid surface. Depending on selection of the fermentation medium, the introduction of the gas bubbles can cause a greater or lesser foam problem. It is absolutely necessary in this case to prevent the foam from being conducted through exhaust gas lines to attached sterile filters and wetting these and thereby causing a contamination risk or a blockage problem. By means of a suitably adjusted wave motion, the foam 49 which is formed on the surface can be drawn into the interior of the medium 4 via flow vortexes 47, 50, in such a manner that, in this case, bursting of the gas bubbles 45 is substantially avoided (FIG. 5d). The foam 49 can thereby be drawn in to an extent in a low-shear manner, in such a manner that the foam thickness is very small or even at least in part the surface is foam-free (FIG. 5e). This is shown by way of example in FIG. 20 in which the foam height h which is formed in the reactor vessel 5 in relation to the mean diameter D is plotted in the region of the surface of the reactor contents 4, wherein the mean diameter results from a round comparison cross section having the same area as the actual cross section of the reactor vessel 5 in the region of the surface of the reactor contents 4. The foam height h relative to the mean diameter D is sketched as a function of the mechanical power input P relative to the volume V of the reactor contents 4. It is shown diagrammatically how the foam height relative to the reactor diameter h/D in the reactor according to the invention (curve 175) at first increases greatly following the gas bubble introduction with an increasing liquid motion caused by the increase of the mechanical power input P/V, in order, however, with a further increase in power input to fall again. Compared with a surface gas introduction reactor without foam-destroying properties (curve 170) in which a continued increase of foam heights with increasing power input can be assumed, a considerably expanded usage spectrum results thereby. In the reactor according to the invention, flow movements having a foam-destroying effect take place, in such a manner that the foam development 175, after passing through a maximum 190 arranged between a first point of inflection 180 and a second point of inflection 185, decreases again. The reactor 5 with at least surface gas introduction can therefore preferably be operated with a specific mechanical power input P/V which, based on the second point of inflection 185, is selected to be greater, so that good mixing performance is possible at a surprisingly low foam development.

In the illustrative example shown in FIG. 5f of the reactor, the housing 6 is suspended so as to be able to rotate via a bearing 8 which is driven by drive 14. The rectangular single-use reactor 43 which is provided with a large lid 250 has a pyramidal base 41, at the bottommost point of which an outlet 42 is provided. In addition to the outflow 42, fluorescence sensors 401, 402 which run in the peripheral direction are provided, which can measure the pH and/or the $O_2$ concentration. For each sensor 401, 402, a light conductor 411, 412 is provided in order to flash the sensors 401, 402 with light for a measurement. Since in the illustrative example shown, the sensors 401, 402 are arranged at the base in the vicinity of the outlet 42, there is the opportunity to construct the sensors 401, 402 as half-ring-shaped sensor layers (FIG. 5g).

A considerable reinforcement of the mixing motion is possible using internals. FIG. 6a and FIG. 6b show by way of example a cylindrical reactor 5 having an installed blade agitator. The blade agitator can be formed by agitator blade film elements 52 which, at the time point of reactor use, are clamped between the two clamping elements 54 and 56. Between 1 and 50, preferably 1-8, particularly preferably 1-4, agitator blade film elements 52 which are distributed uniformly on the periphery, similarly to conventional stirred tanks, are anchored in the central internals 60 and 62. The base bearing 60 is firmly attached by welding or adhesion to the base of the reactor 5 via the support ring 58. Using the drive spindle 59 let into the rotatable base 20, which spindle, depending on the drive moment can be designed, e.g., as a gear wheel or simple key bow, the drive forces are transmitted to the base bearing without transmitting torsion forces to the wall of the reactor 5 which is sensitive in the case of single-use reactors. The clamping of the agitator blade film elements 52 proceeds in single-use reactors in the state of the reactor 5 which is filled with medium 4 by clamping the tie anchor 64 which is connected to the head bearing 62 into the holding device 70, e.g. using a lock nut screw connection 66 and 68 so as to be tight to twisting. The turning moments are transmitted via the holding device 70 to the shell 6 of the supporting container. In this case, a force transmission to the walls of the reactor 5 is avoided. Filling the reactor 5, when it is used as a single-use reactor, is a precondition for clamping the agitator blade film elements 52, when, for the sake of simplicity, additional fastening between the base bearing 60 and the drive spindle 59 is to be omitted.

FIGS. 7a to c show by way of example of the cylindrical reactor 5, which is not restricting to the invention, that, for improving the oxygen introduction, tube modules 72 can relatively simply be accommodated in a reactor 5 as in the mixing appliance shown in FIGS. 6a to c. The module 72 consists, as shown in FIG. 7b, of silicone tubes 74 which are glued in a base body 79 using an FDA-permitted silicone casting composition 78. The base body 79 can be connected gas-tightly to the module holder 80, e.g. using screw connections or, as shown, snap-on connections, wherein the silicone casting compound 78 simultaneously acts as sealing surface. The two channels of the module holder 80 supply the silicone tubes 74 which are laid in two parallel strips, preferably multilayered, with oxygen-containing gas 94, or take care of the removal of the exhausted gas stream 96. Both channels of the module holder 80 are connected via connection elements 82 and 84 to the distribution element 76 which, for the supply of a plurality of modules, provides a distributor space 82 for the gas feed and a distributor space 88 for the exhaust gas. The two distributor spaces 82 and 88 are supported by the coaxial line 90 for gas feed and 92 for gas discharge. The anchoring of the silicone tubes 74, which are laid in a loop-like manner, on the reactor base proceeds using a clamping element 56 laid in the interior of the loop. The silicone tubes are clamped as in the mixing reactor in FIG. 6 in the vessel filled with medium 4. Otherwise, a static connection between base bearing 60 and drive spindle 59 must be supplied. The gas-introduction module 72 can be attached firmly, in particular pneumatically, by an applied reduced pressure, via a base support 58 on the base 20, as a result of which sufficient stability may be achieved to ensure relative motion of the silicone tubes 74 to the medium 4. For this, the base support 58 can lie adjacent to a suction cup 66, wherein the suction cup 66 can be designed as a recess of the housing 6, which recess can be connected to a source of reduced pressure.

FIGS. 8a to 8c show an alternative reactor design which is particularly advantageous compared with the mixing reactor in FIGS. 6a to c, by way of example of a cylindrical reactor 5 which does not restrict the invention to this reactor. The transfer of the rotary oscillation 15 to the medium 4 in this case no longer proceeds via agitator blade film elements 52 which are to be clamped tightly, but by means of pocket-like, welded-in or glued-in invaginations 100 which, as shown, can be used preferably in the base, but also in the head (not shown in the figure) or in the sides (see FIG. 13) of the reactor 5. The static support elements 102 which are mounted on the base 20 can be introduced into the invaginations 100. Mixing elements can proceed in this manner even in empty reactors 5 by simple raising. Reactor and reactor frame consisting of shell 6 and base 20 can thereby be considerably simplified in construction, since with a sufficient number of invaginations, force can be transmitted directly to the reactor 5 without strength problems. Anchoring of the base bearing is omitted. A holding device 70 similar to FIG. 6a is only necessary when invaginations 100 and support element 102 are intended to be used in the head of the bag. For improving the axial mixing, the angle 104 of the support elements may be altered. Better axial mixing is achieved with angles of attack 104 <90°, preferably 30° to 70°, particularly preferably 45° to 60° to the horizontal. If in the case of angles of attack <90° the distance from the reactor wall is to be kept constant, a curved profile for the support element 102 is selected.

In FIG. 9, the conical embodiment of the support elements which is particularly to be preferred for simplified assembly is shown. In this case the shape of the support elements can be pyramidal 110 or conical 108. Since the conical support elements 108 and invaginations 106 are simpler to fabricate, this is considered a preferred solution. Angles 107 between 0° and 45° lead to technically logical solutions, wherein the range between 2 and 15° is to be considered as a particularly preferred embodiment.

Using the arrangement in FIG. 10, by way of the example of a cylindrical reactor 5, but not being restricted to this reactor, the invention shows how by means of UVC irradiation, sterilization or virus inactivation of a medium 4 can be carried out in a reactor 5. In this case not only the reactor 5 and the invaginations 106, but also the support elements 117 and the irradiation shell 114 are fabricated from materials which are transmissive to UVC rays. Materials which come into consideration for the bags are films which are transmissive to UVC rays which are known to those skilled in the art. A certain absorption by the plastic material can be compensated for without problems by the very large irradiation surface which can be achieved in this reactor. The transparent supporting element 117 and the transparent double-wall irradiation shell 114 which is radiation-isolated from the outside, which are fabricated from stable UV-radiation-transmissive materials which are known to those skilled in the art, preferably of quartz glass, Makrolon or PMMA, can be equipped from the interior with UVC radiation sources 116 which are supplied with electrical energy, for example via the base 20.

In FIGS. 11a to e by way of the example of a rectangular reactor 43, but not restricting the invention to this reactor, preferred embodiments and processes of a novel single-use freezing and thawing concept are presented. The drive and energy supply part of the novel reactor is shown in FIG. 11a. The heating/cooling medium 120 is fed via the flexible connection 122 close to the center into a distributor channel 124 of the moving base 20 and subsequently into the flow-passing support elements 127 and the vessel shell 128. The cylindrical reversing device 129 which is installed in the vessel shell 128 ensures targeted upwards-directed overflow of the surface of the heating/cooling shell 128 which is available for heat exchange. The heating/cooling medium flowing downwards in counterflow from the heating/cooling shell 128 is removed on the outside of the heating/cooling shell 128. This is connected to the collection channel 130 via which the heating/cooling medium streams taken off from the support elements 127 via the takeoff tubes 126 are also removed. The collection channel 130 is connected close to the center to the flexible outlet line 132 via the heating/cooling medium 134 which is being changed calorically and recirculated, e.g., into a heat circuit.

In FIG. 10b, the rectangular reactor 43 is shown having invaginations 106 for receiving the support elements 127. The reactor 43, in the head region, has a glued-on or welded-on stable carrier ring 136 to which a plurality of eyes for receiving pulling devices 140 (see FIG. 11*c*) are attached. Using the carrier ring 136 and the pulling appliance 140, the rectangular reactor 43 together with the frozen product can be withdrawn for intermediate storage or returned again to the reactor for thawing. In order to prevent damage to the internal flanks of the invaginations 106 during introduction of the frozen products into relatively large vessels, the use of a carrier construction shown in FIG. 11*d* is advisable. This consists of a thin-walled intermediate base 142 produced from readily heat-conducting materials and conical intermediate elements 148 which are readily heat conducting and as thin-walled as possible, which are placed between the invaginations 106 and the heated/cooled support elements 127. In the center of the base plate there is located an elongated support element 146 having a carrying eye, using which the reactor can be removed by means of a pulling device, e.g. after the freezing process (see FIG. 11*e*). For use of the carrier construction, it is necessary to construct the reactor 43 in the center having a passage 144 instead of an invagination 106. The rectangular shape of the reactor 43 favors space-saving storage and therefore is a particularly preferred embodiment. The carrier construction, furthermore, makes possible damage-free transport (see FIG. 11*d*) of the reactors 43 on a transport base 147 e.g. to a storage space, and simple and hazard-free stacking of the reactors 43 on shelves.

In FIGS. 12*a* to *c*, a preferred embodiment of the mixing reactor which is not restrictive to the invention, having process-intensifying properties for particle retention is presented. The invaginations 150 fabricated, for example, from woven cloth, nonwovens, perforated films, porous layers and/or filter membranes are pulled onto liquid-distributing support elements 148, e.g. gap screens, or perforated sheets. The invagination can be sealed by means of an O-ring 149 in the region of the cylindrical attachment elements 151 fabricated from impermeable materials. The filtrate can be withdrawn via the base 20. The device, in a similar embodiment, is also suitable for liquid distribution, sparging and carrying out reactive process steps at and/or in permeable, semipermeable or non-permeable membranes 150.

In FIGS. 13*a* and *b*, preferred reactors 5 which are not restricting the invention are shown having side pockets 103 integrated into the reactor wall. In this form, the reactor, preferably supported by the side support elements 99 in the outer wall 6, can transmit the rotary motion to the reactor contents in a similar manner to the conventional agitator systems. Support elements 99 and pockets 103 can be used as in the preceding examples, likewise for process intensification. The number, breadth 97 and depth 98, and also the desired material properties (radiation-transmissive, filtering, gas- or heat-permeable) and thereby the material of the side pockets 103 and the side support elements 99 are established by the required boundary conditions, e.g. at the required exchange area. In pure mixing tasks, in a similar manner to agitator systems which are close to the wall, 1 to 8 pockets appear to be sufficient, wherein 2 pockets because of the comparatively low installation expenditure are considered a preferred number. The depth 98 of the pockets 103, in a similar manner to agitator systems, is preferably between 0.02-0.4, preferably 0.05-0.2, particularly preferably 0.1-0.15 times the reactor diameter. The preferred shape of the pockets extends from parallelepipedal via truncated cone to rooflike. The preferred opening angles 97 of the pockets 103 to the support element 99 can in this case vary between 0° and 45°, wherein the opening angles between 2° and 200 are counted as among the preferred angles. The intensity of the axial mixing can be influenced by the angle of incidence 105 of the pockets 103 to the vertical. Expedient angles of incidence are between 0° and 75° and particularly preferably between 0° and 45°.

In the illustrative example of the reactor shown in FIG. 14*a*, the reactor vessel 5 which is constructed as a single-use bag has two bag halves 200 which can be stuck to a frame 201 which is arranged between the bag halves 200. Since the bag halves 200 are constructed so as to be flexible and the frame 201 is constructed so as to be rigid, it is advisable that the housing 6 has grooves 202 into which the projecting part of the frame 201 between the bag halves 200 can be inserted (FIG. 14*c*). Motion of the housing 6 can be directly transmitted to the reactor vessel 5 without a significant friction-burdened relative motion being able to occur. In addition, between an upper holding profile and a lower holding profile of the frame 201, at least one, in particular film-like, or more stable blade agitator 52, if appropriate fabricated from the material of the frame 201, can be provided (FIG. 14*b*). The distance 205 between the blade agitator 52 and the vertical parts of the frame 201 is, in particular, selected in such a manner that slots result which additionally increase vortexing of the medium 4. The distance 205 preferably extends from 0 to 30% of the reactor diameter.

In the illustrative example of the reactor shown in FIG. 15*a* compared with the illustrative example shown in FIG. 14*a*, instead of the blade agitator 52, a gas-introduction module constructed as tube module 72 is provided, wherein the frame 201 can be part of the tube module 72, for example in order to clamp the membrane constructed as permeable silicone tubes 74. The gas stream feed 94 and/or the gas stream outlet 96 can be sealed in a sterile manner before installation of the reactor vessel 5 (FIG. 15*d*) and, after installation (FIG. 15*e*) a gas supply can readily be attached. The supply lines of the gas stream feed 94 and/or of the gas stream outlet 96 can each be arranged completely within a bag half 200 assigned to them, in order not to impair the connection of the bag halves 200 to the frame 201 (FIG. 15*c*). As a result, it is possible to restrict the number of connections passing out of the single-use reactor to the outside and to position them in the vicinity of the vertical axis for gentle handling of the connection lines.

In the alternative embodiment of the membrane 74 shown in FIG. 16*a*, a membrane case 300 is provided which is connected in a two-dimensional manner to a porous layer 301, wherein the porous layer can have an open-pore material, such as, for example, foam material. In order to charge the membrane 74 with a gas pressure, the gas stream feed 94 and/or the gas stream outlet 96 extend from the end side of the membrane 72 (FIG. 16*a*) and/or from the longitudinal side of the membrane 72 (FIG. 16*b*) through the membrane film 300 into the porous layer 301. The membrane 72 has, in particular, two membrane cases 300, which overlap the porous layer 301, in such a manner that the membrane cases 300 can be connected to one another at the overlapping regions and the porous layer can be completely encased (FIG. 16*c*). As a result, a flat membrane 72 can be provided which does not inflate under pressure and, as a flat membrane element 320, can be part of a membrane stack 340, wherein, preferably, all flat membrane elements 320 of the membrane stack 340 are connected to exactly one gas stream feed 94 and/or exactly one gas stream outlet line 96 (FIG. 17*c*). The flat membrane element 320 can be spaced from one another via distancing elements 343 and, as part of the membrane stack 340, be part of the gas-introduction module 72 (FIG. 17*a*). By limiting elements 342, the membrane stack 340 can be fixed in a variable manner on an upper holder 321 and/or a lower holder 322.

In the embodiment of the reactor shown in FIG. 18, the flat membrane 72 is constructed so as to be particularly long and conducted to and fro in a meander-like manner between the lower holder 321 and the upper holder 322, so that a membrane element 350 clamped in a meander-like manner results.

The reactor shown in FIG. 19 has a reactor vessel 5 constructed as a single-use bag which conforms to an inner wall of a moving housing 6. A membrane element 360 is integrated into the bag wall of the reactor vessel 5 in such a manner that the inside of the reactor vessel 5 is lined at least in part with the membrane element 360 in order to be able to introduce gas into the medium 4 from the outside radially also. The gas stream feed 94 and/or the gas stream outlet 96 for the membrane elements 360 can be conducted via the frame 201, in such a manner that further membranes 72 for gas introduction into the medium 4 can be connected without problems to the frame 201.

By means of the process-intensifying internals and thereby the physical, biological, biochemical and chemical reactions which can be carried out in and on membranes, e.g. for gas introduction, gas distribution, liquid distribution, particle retention, irradiation and/or heat feed and removal, the application limits of existing single-use technologies are considerably extended, so that the novel reactors can also be employed on considerably greater scales than those previously available.

The invention claimed is:

1. A reactor comprising a reactor vessel and a drive unit, wherein contents of the reactor vessel are rotated in periodically opposite directions about a fixed vertical axis of the reactor vessel by the drive unit, wherein a mechanical power input from the drive unit into the reactor vessel contents is enabled by a member of the group consisting of a shell form of the reactor vessel having a polygonal cross section at least in a region of the surface of the reactor contents and mixing elements fixed within the reactor vessel, the reactor being a sparged reactor, wherein the reactor vessel has a polygonal cross section at least in a region of a liquid surface of reactor contents taken up by the reactor vessel, which reactor contents are charged with gas bubbles via the surface or porous membranes and, for the purpose of foam destruction, are rotated in opposite directions in a periodic fashion such that foam on a surface of the reactor contents is transported into an interior of the reactor contents.

* * * * *